(12) United States Patent
Sokol

(10) Patent No.: US 8,414,468 B2
(45) Date of Patent: Apr. 9, 2013

(54) ANAL SLING SYSTEM AND METHOD TO TREAT FECAL INCONTINENCE

(76) Inventor: Eric Sokol, Menlo Park, CA (US)

( * ) Notice: Subject to any disclaimer, the term of this patent is extended or adjusted under 35 U.S.C. 154(b) by 633 days.

(21) Appl. No.: 12/646,504

(22) Filed: Dec. 23, 2009

(65) Prior Publication Data

US 2011/0046436 A1 Feb. 24, 2011

Related U.S. Application Data

(60) Provisional application No. 61/234,904, filed on Aug. 18, 2009, provisional application No. 61/246,010, filed on Sep. 25, 2009.

(51) Int. Cl.
*A61F 2/04* (2006.01)

(52) U.S. Cl.
USPC .............................................. 600/30; 600/37

(58) Field of Classification Search ................... 600/30, 600/31, 32, 37; 128/897–899
See application file for complete search history.

(56) References Cited

U.S. PATENT DOCUMENTS

| | | | |
|---|---|---|---|
| 6,575,897 B1 | 6/2003 | Ory et al. | |
| 7,131,944 B2 | 11/2006 | Jacquetin | |
| 7,588,598 B2 | 9/2009 | Delorme et al. | |
| 2008/0004487 A1* | 1/2008 | Haverfield | 600/30 |
| 2008/0021265 A1 | 1/2008 | Garbin et al. | |
| 2009/0192346 A1 | 7/2009 | Rosenblatt | |
| 2009/0192347 A1* | 7/2009 | Davila et al. | 600/37 |

FOREIGN PATENT DOCUMENTS

| | | |
|---|---|---|
| JP | 2006/129979 | 11/2004 |
| WO | 2008/085825 | 1/2008 |

* cited by examiner

*Primary Examiner* — Christine Matthews
*Assistant Examiner* — Joshua D Lannu
(74) *Attorney, Agent, or Firm* — Jeffrey Schox

(57) ABSTRACT

A method of implanting an anal sling in a patient having an anal sphincter with a defective portion, including: linking a first point on the anal sphincter and a second point on the anal sphincter, wherein the second point opposes the first point across the defective portion of the anal sphincter and tightening the anal sling across the defective portion of the anal sphincter. In a preferred embodiment, linking the first and second points on the anal sphincter includes passing a first end of the anal sling, coupled to a first-side needle tool, through the anal sphincter at the first point and passing a second end of the anal sling, coupled to a second-side needle, through the anal sphincter at the second point.

36 Claims, 21 Drawing Sheets

ANAL SLING SYSTEM AND METHOD TO TREAT FECAL INCONTINENCE

CROSS-REFERENCE TO RELATED APPLICATIONS

This application claims the benefit of U.S. Provisional Application Nos. 61/234,904, filed 18 Aug. 2009, and 61/246,010, filed 25 SEPT. 2009, which are incorporated in their entirety by this reference.

TECHNICAL FIELD

This invention relates generally to the medical field, and more specifically to an improved anal sling system and method to treat fecal incontinence in the surgical field.

BACKGROUND

Fecal incontinence is a condition in which fecal material is involuntarily excreted or leaked due to decreased bowel control. Fecal incontinence of varying degrees is thought to be a result of any number of factors, including dysfunction of or damage to the anal sphincters, dysfunction of the pelvic floor, decreased compliance in the rectum, impaired sensation in the rectum, and fecal impaction. However, a significant number of women develop fecal incontinence after experiencing anal sphincter tears and/or pudendal nerve trauma during vaginal child delivery. Conventional treatments for fecal incontinence include medical therapy (such as diet changes, supplements, or drugs), and biofeedback therapy (in which a patient is taught to retrain the musculature of the pelvic floor and abdominal wall), but these treatments are often supplemental measures that do not fully treat major incontinence.

A common surgical treatment for fecal incontinence is sphincteroplasty involving overlap repair of the external anal sphincter, which is successful for a portion of patients with damage to the sphincter. Other surgical treatments include transplantation of striated muscle to replace irreversibly damaged sphincter muscles, insertion of a synthetic sphincter device controlled by a hand pump, and a colostomy in which the colon is connected to an opening on the abdominal wall to allow feces to pass through the abdomen. However, these treatments have drawbacks. Sphincteroplasty is a technically challenging procedure, and is not suitable for all patients with sphincter damage, such as those with sphincter defects spanning over 180 degrees of the sphincter perimeter. Furthermore, many sphincteroplasties lead to unsatisfactory results, as the procedure typically requires long incisions that are more susceptible to infection and incision break down, and many sphincteroplasties eventually fail after some time. Transplantation of muscle or insertion of a synthetic sphincter device is relatively invasive and time-consuming, and a synthetic sphincter device is an inconvenient, less than ideal solution that has a high complication and explant rate. A colostomy is also less than ideal, since it is a major, life-changing procedure that is typically performed as a last resort when other treatments have failed or are unsuitable.

The stigma associated with fecal incontinence often leads to shame and problems with self-confidence, resulting in social withdrawal and isolation. Successful and appropriate treatments for fecal incontinence are crucial for maintaining quality of life for patients afflicted with the condition. Thus, there is a need to create an improved treatment for fecal incontinence. This invention provides such an improved anal sling system and method to treat fecal incontinence in the surgical field.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Anal Sling System

Figure 1:
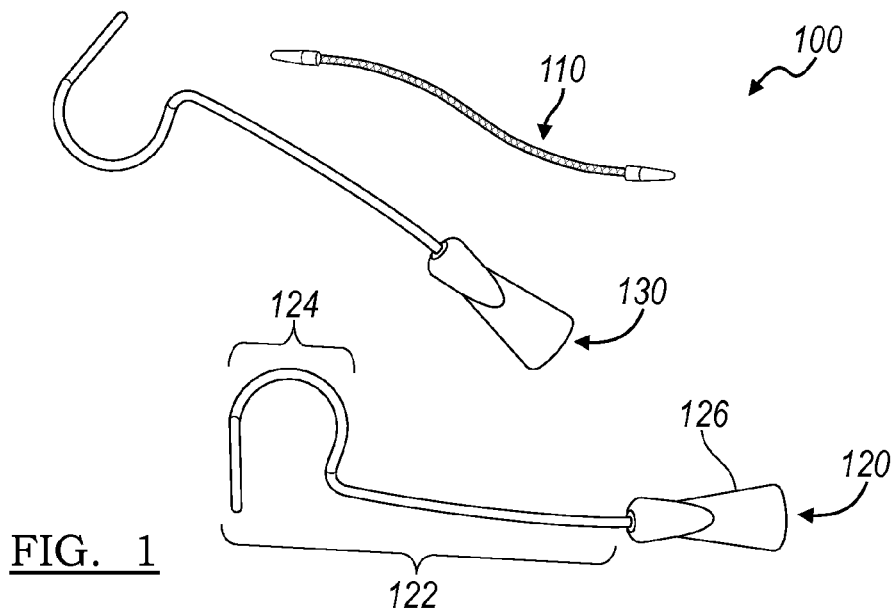
FIG. 1 is a schematic representation of the anal sling system of a preferred embodiment.

As shown in FIG. 1, the anal sling system 100 of the preferred embodiment includes an anal sling 110 that is adapted to be implanted across a defective portion of an anal sphincter of a patient; and a needle tool set including a left-side needle tool 120 that guides implantation of the left side of the anal sling and a right-side needle tool 130 that guides implantation of the right side of the anal sling. The system is preferably used to repair defects of the external anal sphincter (EAS) and/or internal anal sphincter (IAS) that contribute to fecal incontinence, but may alternatively be used in a similar manner to repair defects of other sphincters, and/or for any suitable conditions. The system is preferably used to treat fecal incontinence in a female mammal such as a human, but may alternatively be used to treat fecal incontinence in a male mammal, or any suitable animal with a sphincter.

Figure 2:
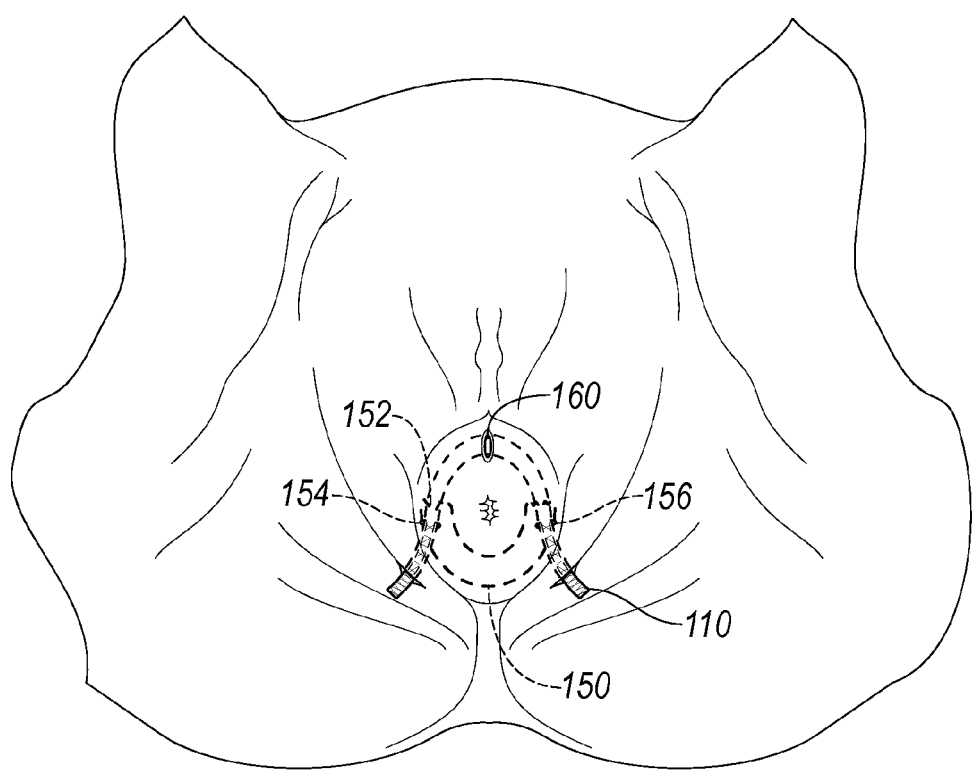
FIG. 2 is a schematic representation of the anal sling implanted in an anal sphincter.
Figure 3A:
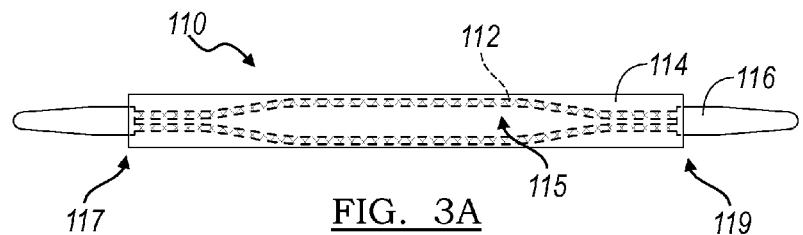
FIGS. 3A and 3B are variations of the anal sling of a preferred embodiment.
Figure 3B:
Figure 4:
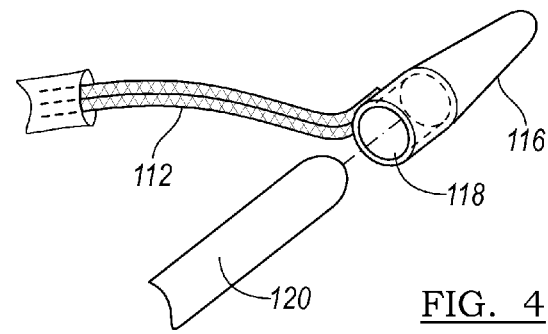
FIG. 4 is an insertion tip of the anal sling of a preferred embodiment.

The anal sling 110 of the system functions to repair a defective portion 152 of an anal sphincter 150, which may be torn and/or otherwise damaged from trauma such as vaginal child delivery, birth defect, or surgical trauma. The sling 110 is preferably designed to replicate the functionality of the defective portion of the IAS and/or EAS, but may alternatively be designed to enhance any suitable sphincter. As shown in FIG. 2, the sling 110 is preferably implanted across a defective portion 152 of an anal sphincter 150, with each end of the sling passed through the anal sphincter muscle (the IAS or EAS, or both). The defective portion 152 is preferably near the perineum of the patient such that the anal sling is a transperineal anal sling that, when implanted, is laid across the perineum, but the defective portion 152 may alternatively be any suitable portion of a sphincter. A first end of the sling is preferably passed through a first point 154 of the anal sphincter and a second end of the sling is preferably passed through a second point 156 of the anal sphincter, such that the second point preferably opposes the first point across the defective portion of the anal sphincter. The sling, when implanted in the patient, is preferably tightened between the first and second points, thereby linking the first and second points, such that the sling supplements the tonic contractions of a nondefective, functional portion of the original sphincter to maintain fecal continence. One sling is preferably implanted, but any suitable number of slings may be implanted as necessary. As shown in FIGS. 3 and 4, the sling of the preferred embodiments includes a mesh strip 112, a sheath 114, and at least one insertion tip 116 on each end of the mesh strip 112.

The mesh strip 112 is preferably an elongated, generally rectangular strip of mesh made of polypropylene or another suitable biocompatible material. The holes of the mesh are preferably large enough to permit passage of macrophages to discourage infection caused by implantation of the sling. The mesh strip 112 is preferably made of a material and/or includes features to allow the sling to be self-fixing in biological tissue. Except as noted below, the mesh strip 112 of the anal sling 110 is preferably similar to mesh strips in urethral slings that are commonly used to treat urinary incontinence, such as that described in U.S. Pat. No. 7,112,171 entitled "Sling assembly with convenient and secure attachment", which is incorporated in its entirety by this reference. The mesh strip 112 may include one piece of material, or multiple pieces of material joined and/or integrated to form one strip. For example, the mesh strip 112 may include two halves, each of which may be implanted separately, that join to form a longer strip. The mesh strip 112 is preferably sized to be implanted in an anal sphincter, with a length sufficient to extend at least from a first side of the sphincter, to a perineal incision 160, and to a second side of the sphincter opposite the first side, and may include additional length to compensate for a variety of anatomical sizes. The mesh strip 112 may be wider, thicker, and/or shorter than a mesh strip typically used in urethral slings, to better enable the mesh strip to withstand higher, sustained tensile forces in the sphincter. The mesh strip 112 may include a tensioning structure, and more preferably an absorbable tensioning structure, which preferably allows more precise tightening of the sling 110 during implantation of the sling. The tensioning structure preferably extends along at least a substantial portion of the length of the mesh strip 112. As an example, the tensioning structure may be an absorbable elastic suture that is threaded into the mesh strip 112, from one end of the mesh strip to the other end of the mesh strip, and knotted near each end of the mesh strip 112. As shown in FIG. 3A, the mesh strip 512 preferably includes a central portion 115 that is wider than the ends 117 and 119 of the mesh strip, and that tapers to the widths of the ends 117 and 119 of the mesh strip. Alternatively, as shown in FIG. 3B, the mesh strip may be of uniform width. At least the middle portion of the mesh strip 512 is preferably wide enough to span both the IAS and the EAS, but may be any suitable width. In one specific embodiment, the mesh sling is approximately 20 cm long and the middle portion of the mesh strip is approximately 2 cm wide. The mesh strip 112 may additionally and/or alternatively be made of a stronger material, include a stronger mesh weave pattern, and/or include any other suitable adaptations to be implanted in the anal sphincter.

The sheath 114 of the sling functions to protect the mesh strip 112 and facilitate smooth movement during implantation of the sling. As shown in FIGS. 3A and 3B, the sheath 114 preferably completely longitudinally encloses or surrounds the mesh strip 112 like a sleeve, but may alternatively partially surround the mesh strip. The sheath 114 preferably includes two pieces that overlap near the central portion of the mesh strip 112, but may alternatively include one piece extending along the length of the mesh strip, or any suitable number of pieces. The sheath is preferably similar to that used in conventional urethral slings, such as that described in U.S. Pat. No. 7,112,171. During implantation of the anal sling 110, the overlapping sheath pieces may be clamped in place relative to the mesh sling, to protect the mesh sling from bacteria and other possible harmful environmental effects. The sheath may include an antibacterial coating to help reduce the likelihood of infection. The sheath 114 is preferably removed after implantation of the sling by pulling the sheath off the mesh strip 112 at one or both ends of the mesh strip or by any other suitable method. However, the sheath 114 may alternatively be made of a biodegradable, absorbable material, similar to that described in U.S. Pat. No. 7,556,598 entitled "Dissolvable protective treatment for an implantable support sling", which is incorporated in its entirety by this reference, or may be constructed in any suitable manner that facilitates removal of the sheath.

The insertion tip 116 of the sling functions to selectively attach an end of the sling to a left-side or right-side needle tool during implantation of the sling. In some embodiments, the insertion tip 116 further functions to pierce and/or burrow through tissue during implantation of the sling. The sling preferably includes two insertion tips, one on each end of the sling, but may alternatively include any suitable number of insertion tips. Each insertion tip 116 is preferably selectively attached to a needle tool before implantation of an end of the sling, and is preferably detached from the needle tool after implantation. Except as described below, each insertion tip is preferably similar to that used in conventional urethral slings, such as that described in U.S. Pat. No. 7,393,320, entitled "Pelvic floor health articles and procedures", which is incorporated in its entirety by this reference. The insertion tip may be pointed and/or have any suitable adaptations for piercing tissue, and may be selectively attached to the sling with a snap fit or threads, and may include a recess 118 for selectively attaching to a needle tool. The insertion tip 116 is preferably shorter and/or narrower than those used in conventional urethral slings, but may be any suitable shape. Similar to self-fixing slings, the insertion tip 116 may also be made of a material and/or include features that allow the insertion tip to be self-fixing in biological tissue.

The needle tool set of the preferred embodiment includes a left-side needle tool 120 and a right-side needle tool 130. The left-side needle tool 120 preferably functions to couple to an insertion tip 116 of the sling and to guide implantation of the left end of the sling into the patient. As shown in FIG. 4, the left-side needle tool 120 preferably couples to the insertion tip 116 by being inserted into a recess 118 of the insertion tip, but may alternatively couple to the insertion tip in any suitable manner. Except as described below, the left-side needle tool 120 is preferably similar to that described in U.S. Pat. No. 7,357,773 entitled "Handle and surgical article", which is incorporated in its entirety by this reference. As shown in FIG. 1 the left-side needle tool 120 preferably includes a needle portion 122 and a handle 126. The needle portion 122 preferably includes a curved portion 124, and more preferably a helical portion. However, the needle portion may alternatively be any suitable shape. The left-side needle tool 120 may alternatively be a self-passing needle driver or a deliverance device for a self-fixating sling insertion tip 116. The right-side needle tool 130 preferably functions to guide implantation of the right end of the sling into the patient. The right-side needle tool 130 is preferably similar to the left-side needle tool 120, except the right-side needle tool 130 is preferably a mirrored version of the left-side needle tool 120, adapted for implantation of the right end of the sling. The left-side needle tool and the right-side needle tool may alternatively be combined into a single, universal-side tool.

2. Method of Implanting an Anal Sling

The method of implanting an anal sling system 200 is preferably used to repair defects of an external and/or internal anal sphincter that contribute to fecal incontinence, but may alternatively be used in a similar manner to repair defects of other sphincters that contribute to any suitable condition. The method is preferably performed to treat fecal incontinence in a female human or other mammal, but may alternatively be used to treat fecal incontinence in a male mammal, or any suitable animal with an anal sphincter. The method can be accomplished with four major variations: "pushing down", "pulling down", "pushing up" and "pulling up", as described below.

2.1 Method of Implanting an Anal Sling—"Pushing Down"

The pushing down variation of the method of implanting an anal sling in an anal sphincter of a patient preferably includes the steps of: linking a first point on the anal sphincter and a second point on the anal sphincter, which includes passing a first end of the sling through the anal sphincter at the first point S210 and passing a second end of the sling through the anal sphincter at the second point S220; and tightening the anal sling across a defective portion of the anal sphincter S230. The first and second points on the anal sphincter are preferably located opposite to one another across the defective portion. The method may also include removing a sheath of the sling S240 and/or closing incisions S250.

Step S210, which includes passing a first end of the sling through the anal sphincter at the first point, functions to implant a portion of the sling in the anal sphincter of the patient. As shown in FIGS. 5A through 5D, in the pushing down variation, Step S210 includes the following four substeps: coupling a first needle tool to a first insertion tip on the first end of the sling S212; passing the first needle tool and first end of the sling into a tunnel that passes through the sphincter S214 at a first point, wherein the first needle tool enters the tunnel at a perineal incision created in the perineum of the patient; decoupling the first needle tool from the first end of the sling S216; and withdrawing the first needle tool to exit out the perineal incision S218.

Figure 5A:
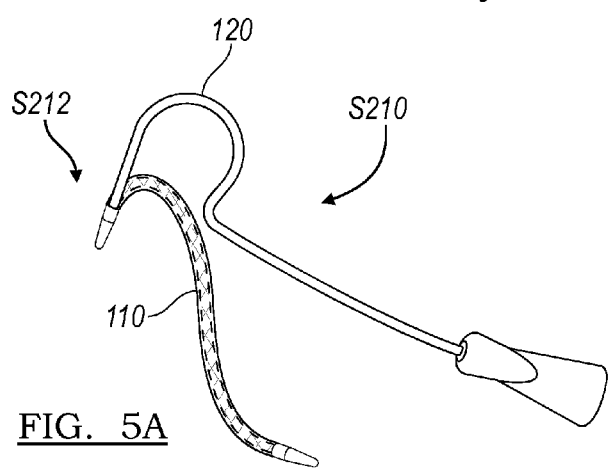
FIG. 5 is an illustration of the step of passing a first end of the sling through a the sphincter at a first point of the pushing down variation of the method of implanting an anal sling.

Step S212 of coupling a first needle tool to a first insertion tip functions to secure the sling to a structural backbone that directs the sling during implantation. The sling preferably includes a removable sheath that surrounds at least a portion of the length of the sling, at least one insertion tip coupled to the sling at each end of the sling, and is preferably similar to conventional urethral slings, as mentioned above. The needle tool preferably includes a helical shape and is preferably adapted for use with either a left hand or a right hand. However, the needle tool may alternatively be any suitable shape, and/or adapted for use with both a left hand and a right hand. As shown in FIG. 5A, the needle tool preferably securely attaches to the insertion tip in a removable manner, such as being removably inserted in a recess of the insertion tip, to allow the needle tool to be separated from the sling after implantation of the first end of the sling, but the needle tool may alternatively permanently attach to the insertion tip.

Figure 5B:
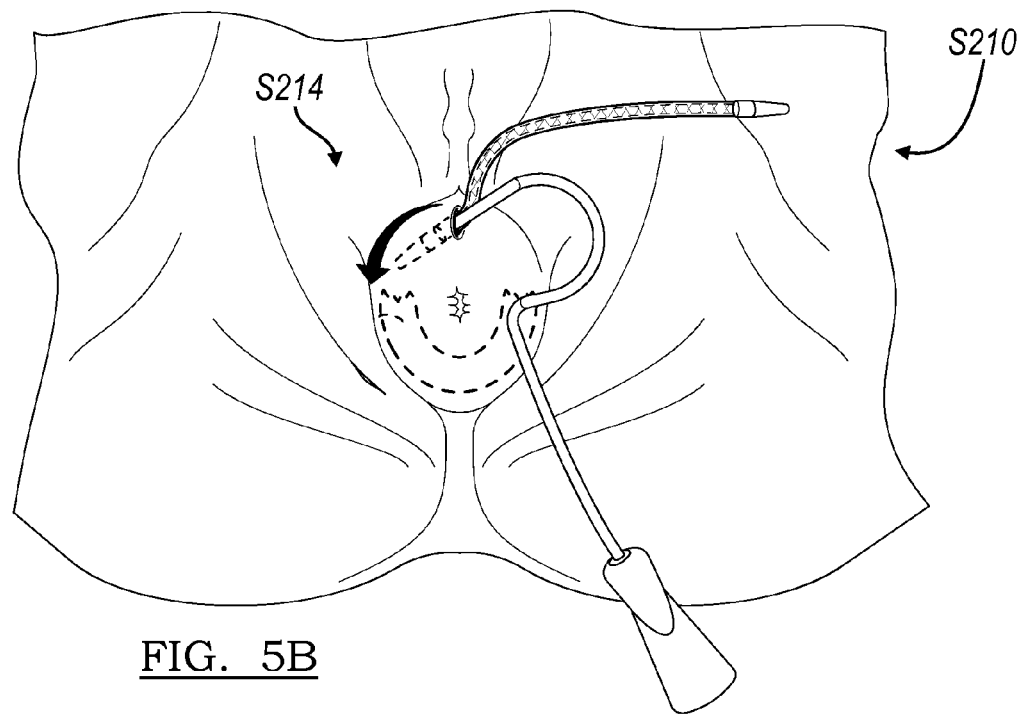
Figure 7:
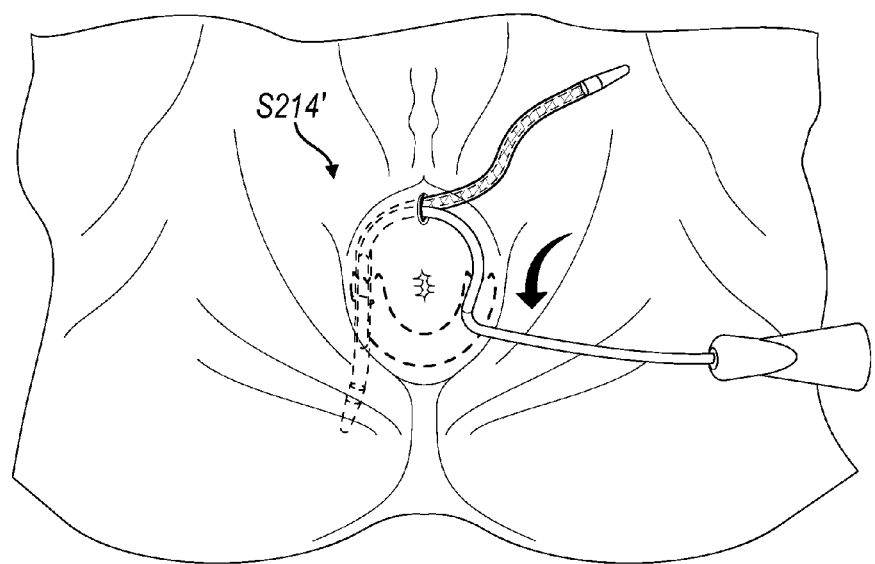
FIG. 7 is an illustration of an alternative substep of the step of passing a first end of the sling through the sphincter of the pushing down variation of the method of implanting an anal sling.

Step S214 of passing the first needle tool preferably functions to attach the sling to the sphincter at the first point by pushing the first end of the sling through the tunnel through the anal sphincter. The anal sling is preferably handled to avoid contact with possible sources of contamination, such as the anus. The first point is preferably in a normal, functional portion (relative to the defective portion) of the sphincter, and more preferably at an end of the functional portion of the sphincter. However, the first point may be on one side of the defective portion (such as near an edge of the defective portion) or in any suitable location. An end of the functional portion of the sphincter may be identified and marked prior to execution of the method, such as with an endoanal ultrasound (EAU) probe and/or a finger inserted into the rectum, in a clinic before surgery and/or immediately prior to execution of the method. An end of the functional portion of the sphincter may additionally and/or alternatively be identified and marked with an EAU probe and/or finger during performance of the method. As shown in FIG. 5B, the perineal incision forming the entrance of the tunnel is preferably surgically created at the anterior portion of the perineum, and the buttock incision forming the exit of the tunnel is preferably surgically created approximately 3 cm lateral and 3 cm posterior to the sphincter. Alternatively, the perineal incision may be created at the posterior fourchette of the vagina. These incisions allow access to the external anal sphincter muscle while helping to avoid damage to the inferior rectal branches of the pudendal nerve and/or other crucial tissue. However, the tunnel may extend between incisions in any suitable locations, and the tunnel may be any suitable position and orientation depending on the specific application. Furthermore, as shown in FIG. 7, in a variation of the step of passing the first needle tool S214', the tunnel may lack an exit incision and end within the body after passing through the sphincter at the first point. For example, the tunnel may begin at the perineal incision or vaginal incision, pass through the sphincter, and end without a buttock incision. A portion of the tunnel, preferably between the perineal incision and just before puncture of the sphincter, is preferably surgically created in preparation of execution of the method, using electrocautery surgical technique or any suitable technique. The entire tunnel may additionally and/or alternatively be surgically created in preparation of performance of the method. At least a portion of the tunnel may additionally and/or alternatively be created during the step of threading the end of the sling through a tunnel, with a cutting instrument located on the insertion tip of the sling. The cutting instrument may be a blade, point or other suitable cutting instrument on the insertion tip, and/or a portion of the needle tool that extends through the insertion tip, and/or any suitable cutting instrument.

Figure 5C:
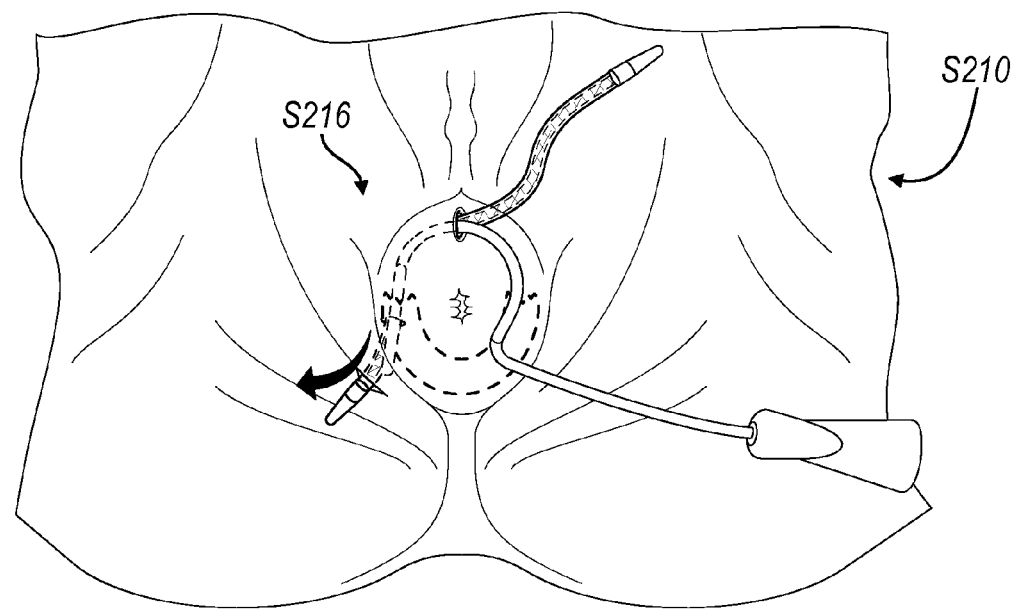

Step S216 of decoupling the first needle tool from the first end of the sling preferably functions to free the first needle tool from the sling in preparation for withdrawal of the first needle tool. As shown in FIG. 5C, the step of decoupling the first needle tool from the first end of the sling preferably includes decoupling the first needle tool from the first insertion tip such as by removing the needle tool from the recess of the insertion tip or any suitable step. However, the step of decoupling the first needle tool from the first end of the sling may alternatively include detaching the first insertion tip from the first end of the sling, which may be accomplished by decoupling a suitable fastener or mechanism, and/or by trimming the coupled first needle tool and first insertion tip from the sling with scissors, a blade, or any suitable cutting instrument.

Figure 5D:
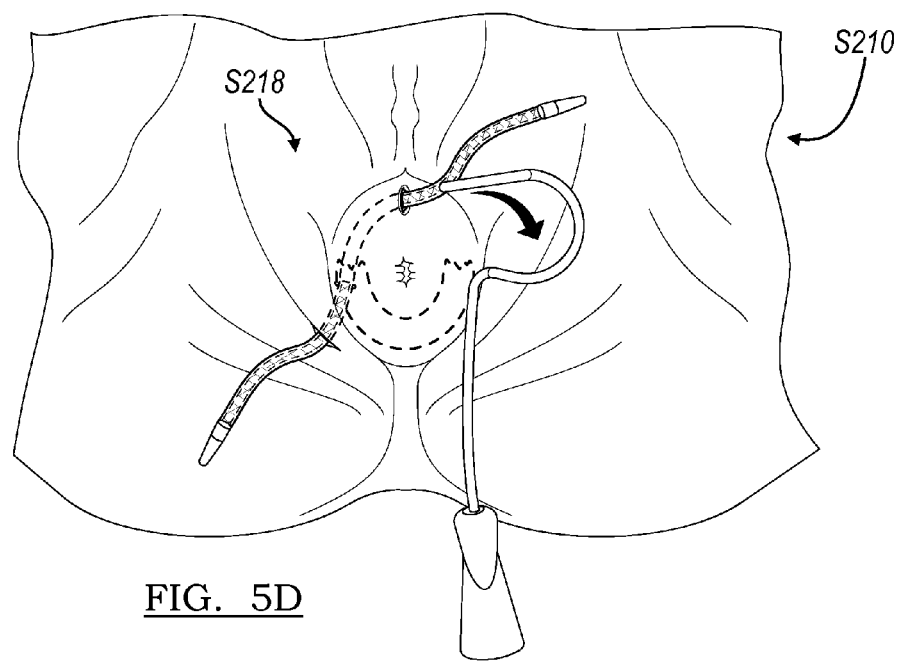
Figure 6A:
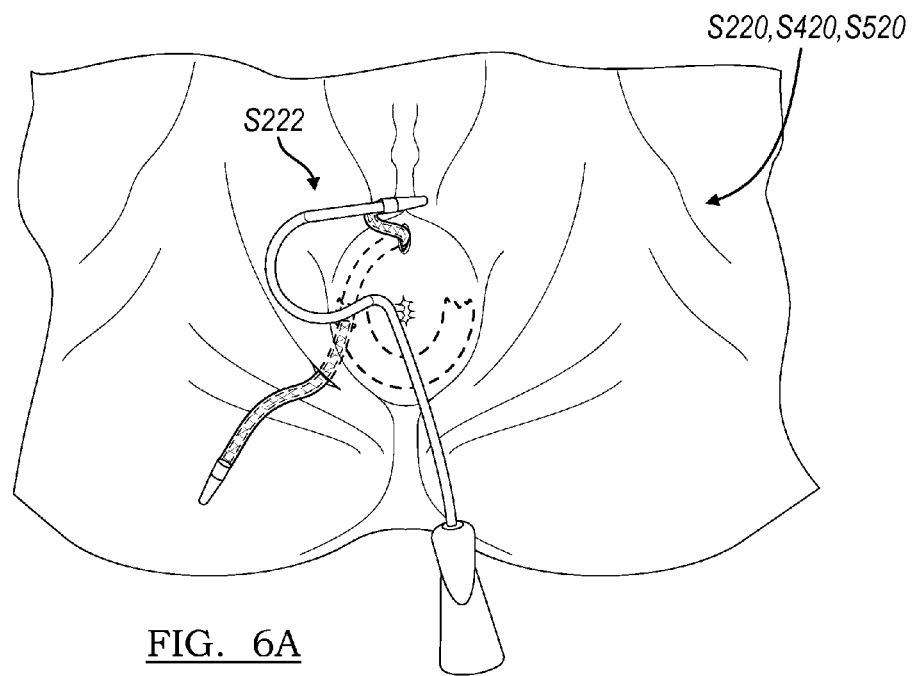
FIG. 6 is an illustration of the step of threading a second end of the sling through the sphincter at a second point of the pushing down variation of the method of implanting an anal sling.
Figure 6B:
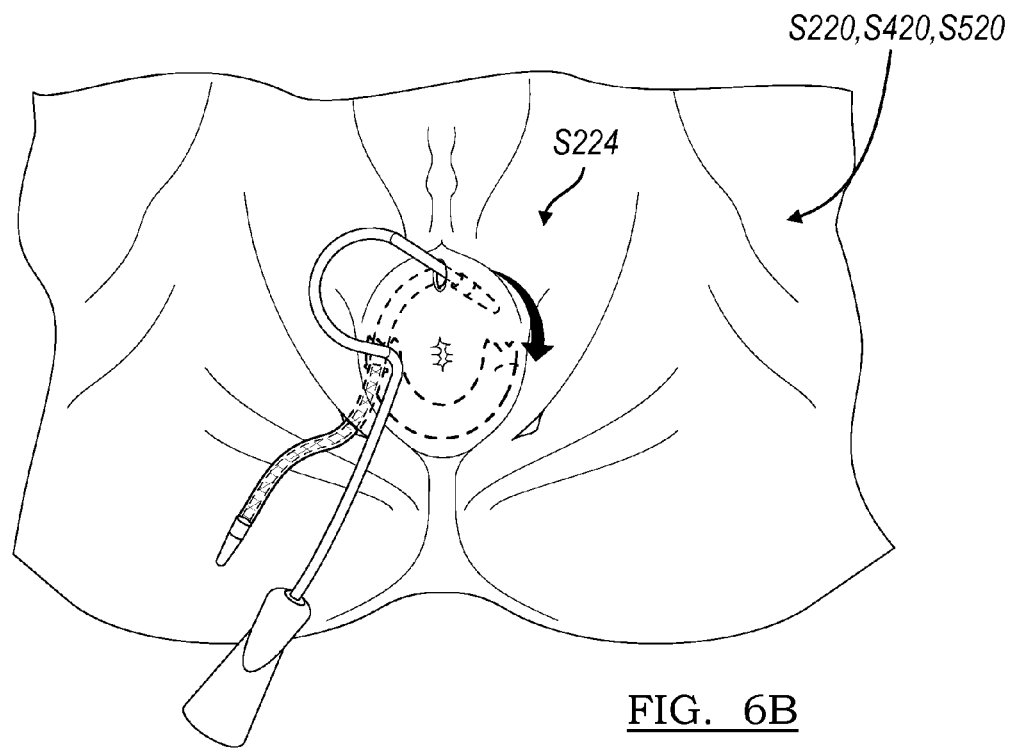
Figure 6C:
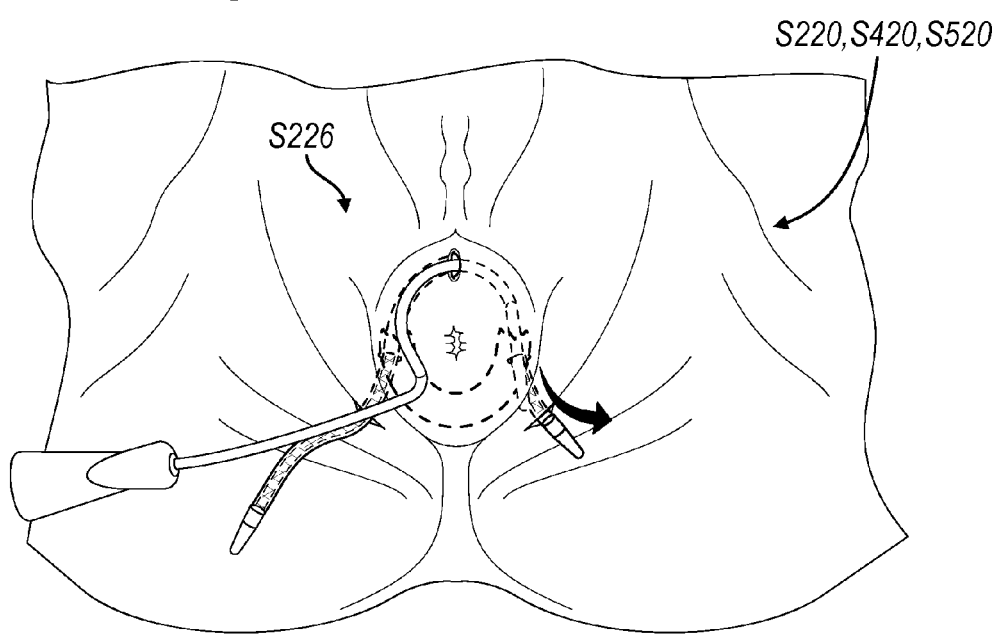
Figure 6D:
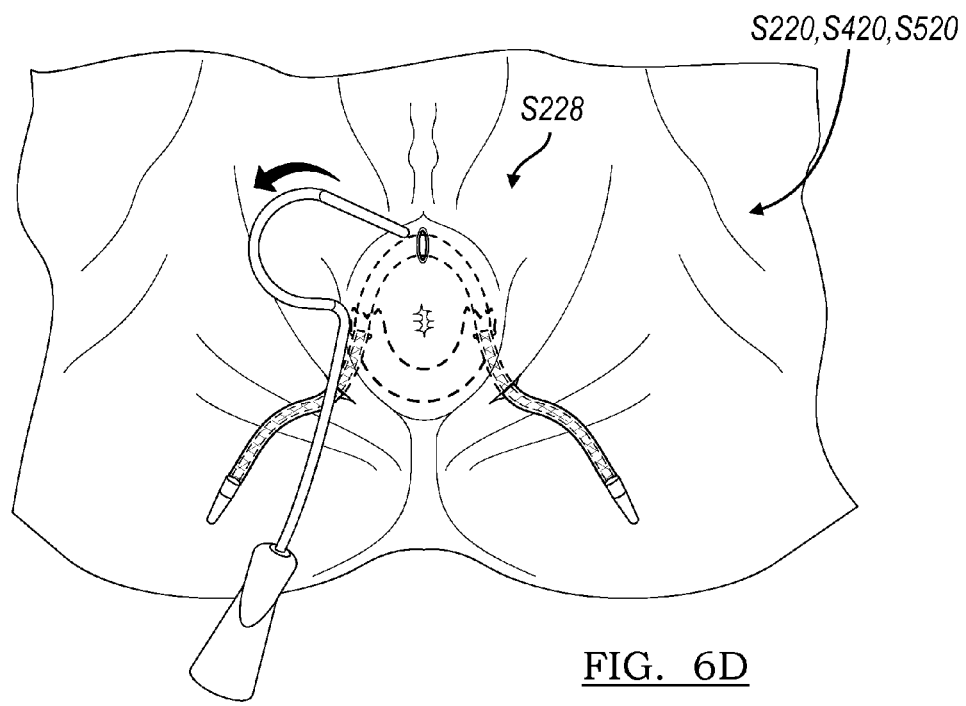

Step S218 of withdrawing the first needle tool to exit out the perineal incision preferably functions to remove the first needle tool from the patient. As shown in FIG. 5D, the first needle tool is preferably passed through the tunnel in a direction reverse of that in Step S214, to exit from the perineal incision and leave behind the implanted sling.

Figure 8:
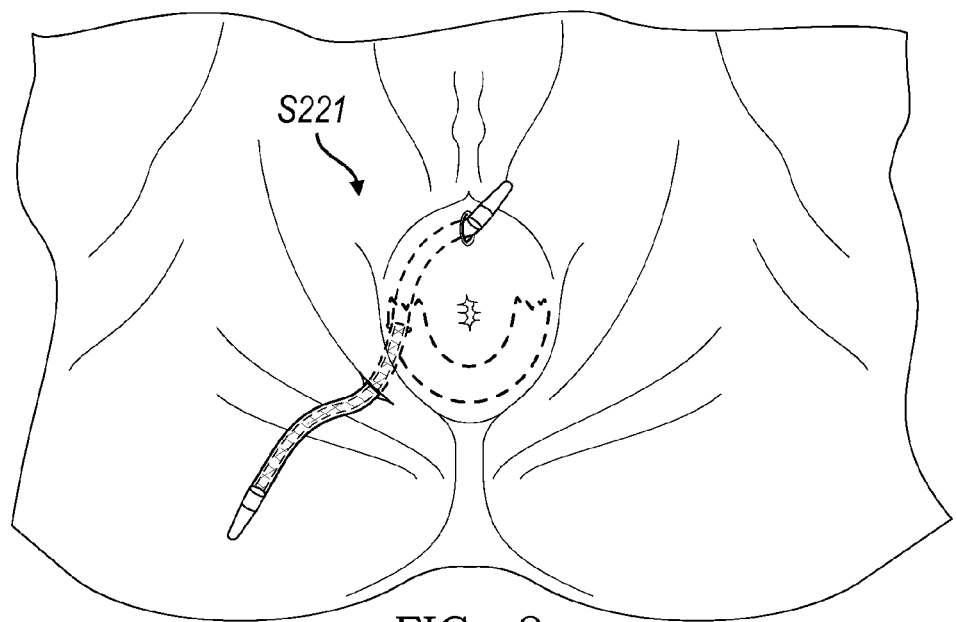
FIG. 8 is an illustration of the step of positioning the sling such that the second end of the sling is near the perineal incision of the method of implanting an anal sling.

Step S220, which includes passing a second end of the sling through the anal sphincter at a second point, functions to implant a second portion of the sling in the anal sphincter of the patient. The second point is preferably opposite the first point, across the defective portion, and preferably on another end of the functional portion of the sphincter. However, the second point may be on one side of the defective portion (such as near an edge of the defective portion) or in any suitable location. As shown in FIGS. 6A-6D, in the pushing down variation, the step of passing a second end of the sling includes the following four substeps: coupling a second needle tool to a second insertion tip on the second end of the sling S222; passing the second needle tool and second end of the sling into a second tunnel that passes through the sphincter at a second point S224, wherein the second needle tool enters the tunnel at a perineal incision created in the perineum of the patient; decoupling the second needle tool from the second end of the sling S226; and withdrawing the second needle tool to exit out the perineal incision S228. Steps S222, S224, S226, and S228 are preferably similar to S212, S214, S216, and S218, respectively, except Steps S222, S224, S226, and S228 are preferably mirrored versions of Steps S212, S214, S216, and S218, respectively. The perineal incision at one end of the tunnel created and used in step S224 may be identical to the perineal incision of step S214, or may be a different incision. As shown in FIG. 8, the step of passing a second end of the sling S220 may include adjusting the sling position S221 such that the second end of the sling is near the perineal incision, to allow insertion of the second end of the sling into the tunnel without requiring a very small bend radius of the sling and/or risking damage to the sling.

Figure 9:
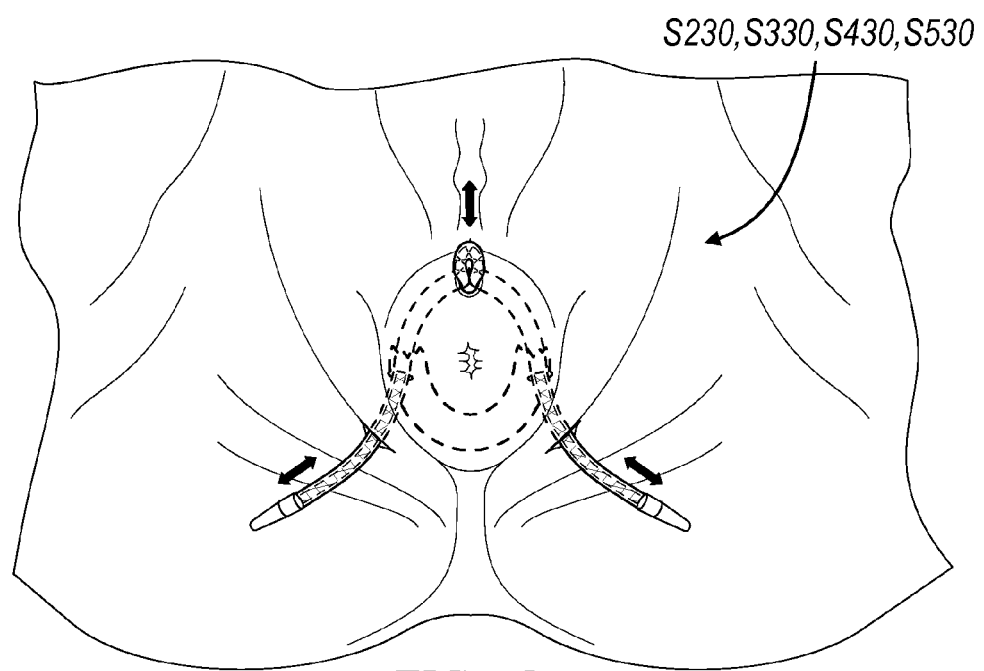
FIG. 9 is an illustration of the step of tightening the sling of the method of implanting an anal sling.
Figure 10:
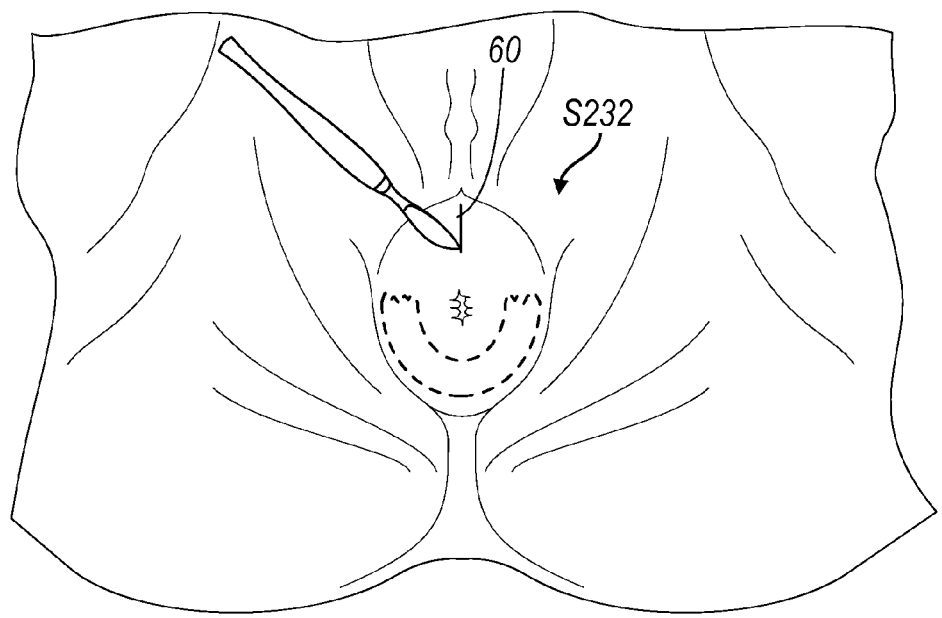
FIG. 10 is an illustration of the step of widening the perineal incision of the method of implanting an anal sling.
Figure 11:
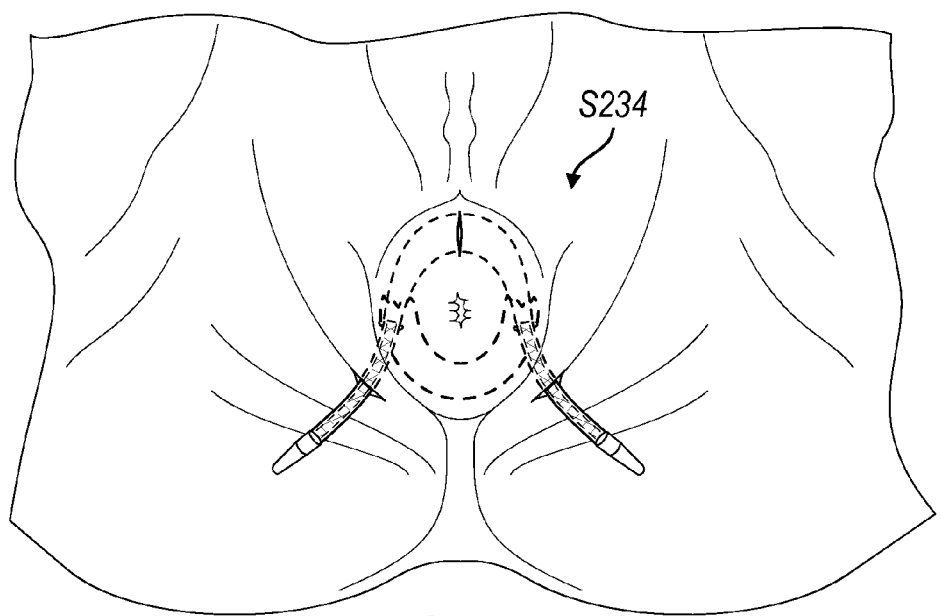
FIG. 11 is an illustration of the step of laying the anal sling flat over the anal sphincter in the perineal incision of the method of implanting an anal sling.

Step S230, which includes tightening the anal sling across the defective portion of the anal sphincter, functions to adjust the tension in the sling, the position of the sling, and/or other aspects of fit of the sling to allow the sling to properly supplement contraction of the sphincter. The sling is preferably tightened until it lies flat on the sphincter. The sling is preferably adjusted to have minimal slack, such that the contraction of the external anal sphincter sufficiently contracts the sling to improve fecal continence, and the sling is preferably adjusted to not have excess tension, such that the tightness of fit does not obstruct passage of feces when the sphincter relaxes. As shown in FIG. 9, the step of tightening the anal sling may include pulling the first end of the sling, pulling the second end of the sling, and/or pulling an exposed portion of the sling in the incision of the perineum, as required to obtain the proper fit adjustment of the sling. Pulling the first end of the sling and pulling the second end of the sling function to tighten the fit of the sling, and pulling the portion of the sling accessible through the incision of the perineum functions to loosen the fit of the sling. The step of tightening the anal sling may include inserting a finger in the anus to feel for an appropriate tightness or other fit of the sling. As shown in FIGS. 10 and 11, the step of tightening the anal sling may also include the step of widening the perineal incision S232, preferably such that the width of the perineal incision is approximately equal to the width of the anal sling, and the step of laying the anal sling flat on the anal sphincter in the perineal incision S234. Steps S232 and S234 may be performed iteratively such that the perineal incision is progressively widened in trial and error to allow the anal sling to lie flat on the sphincter muscle within the perineal incision. However, steps S232 and S234 may alternatively and/or additionally be performed at any time during the method, such as before passing the first end of the sling, or before passing the second end of the sling.

Figure 12:
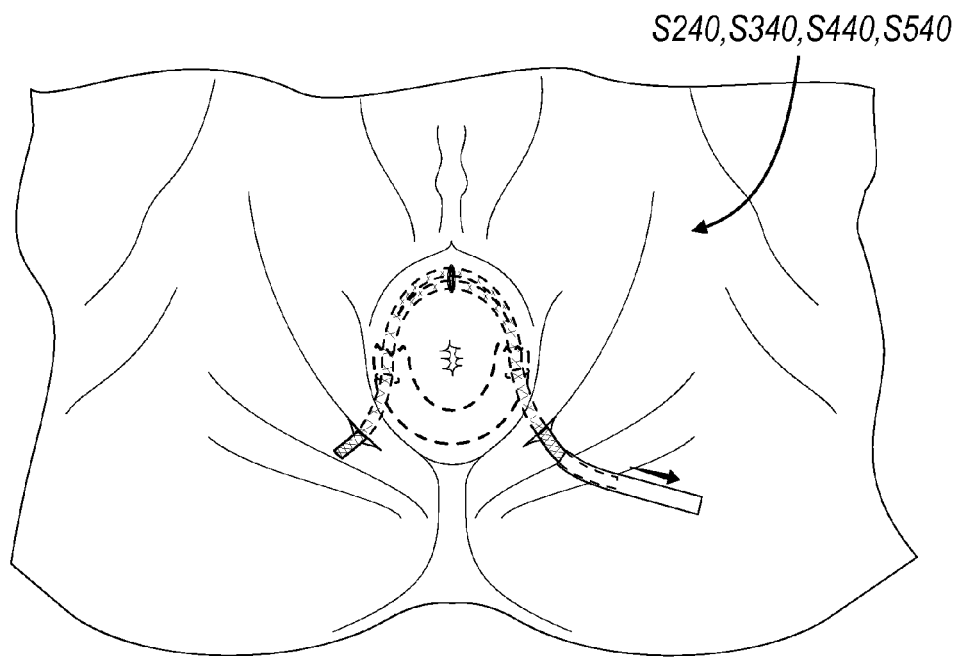
FIG. 12 is an illustration of the step of removing the sheath of the sling of the method of implanting an anal sling.

The method may further include Step S240, which includes removing a sheath from the sling and functions to allow the sling to become fixated in the patient. As shown in FIG. 12, the step of removing the sheath from the sling preferably includes pulling the sheath off the sling at one of the buttock incisions, which enables the sling material to self-fixate to tissue. The step of removing the sheath from the sling may include pulling the sheath off the sling at both buttock incisions, such as if the sheath is made of two or more separate pieces. Removing the sheath from the sling may additionally and/or alternatively include allowing the sheath to dissolve in the body, if the sheath includes a biodegradable, absorbable material. Removing the sheath from the sling may additionally and/or alternatively include removing the first and second insertion tips of the sling.

Figure 13:
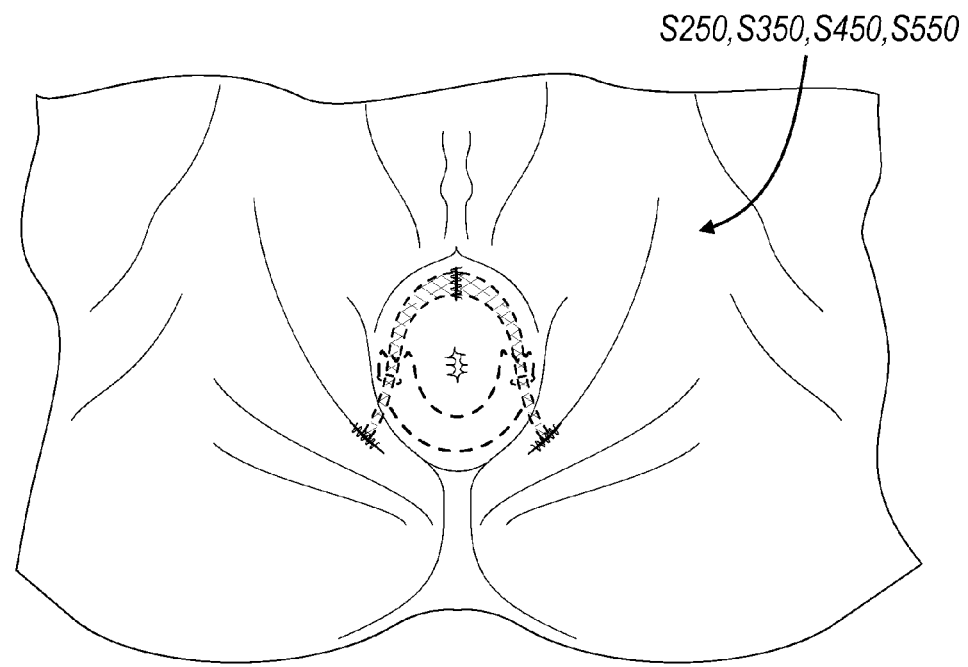
FIG. 13 is an illustration of the step of closing incisions of the method of implanting an anal sling.
Figure 14A:
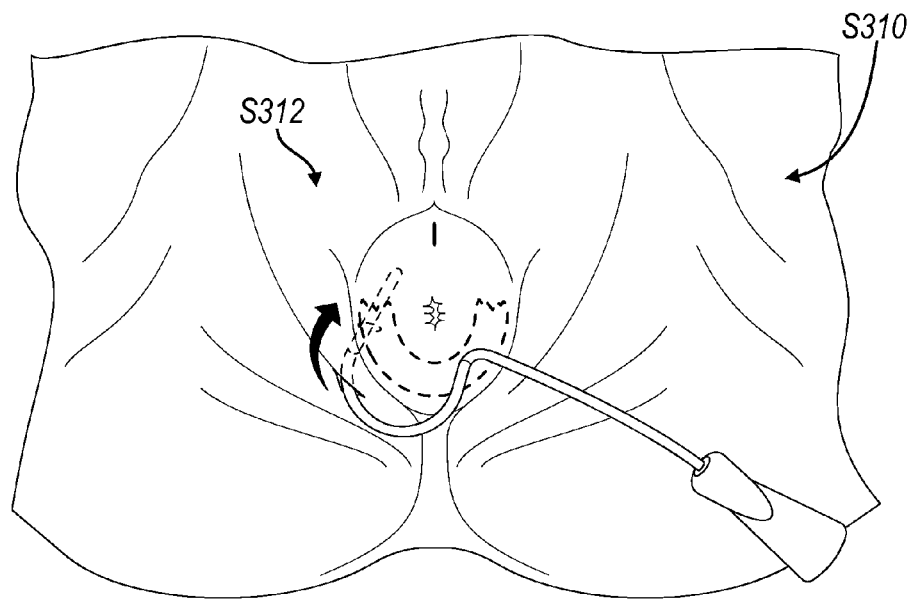
FIG. 14 is an illustration of the step of passing a first end of the sling through the sphincter at a first point of the pulling down variation of the method of implanting an anal sling.
Figure 14B:
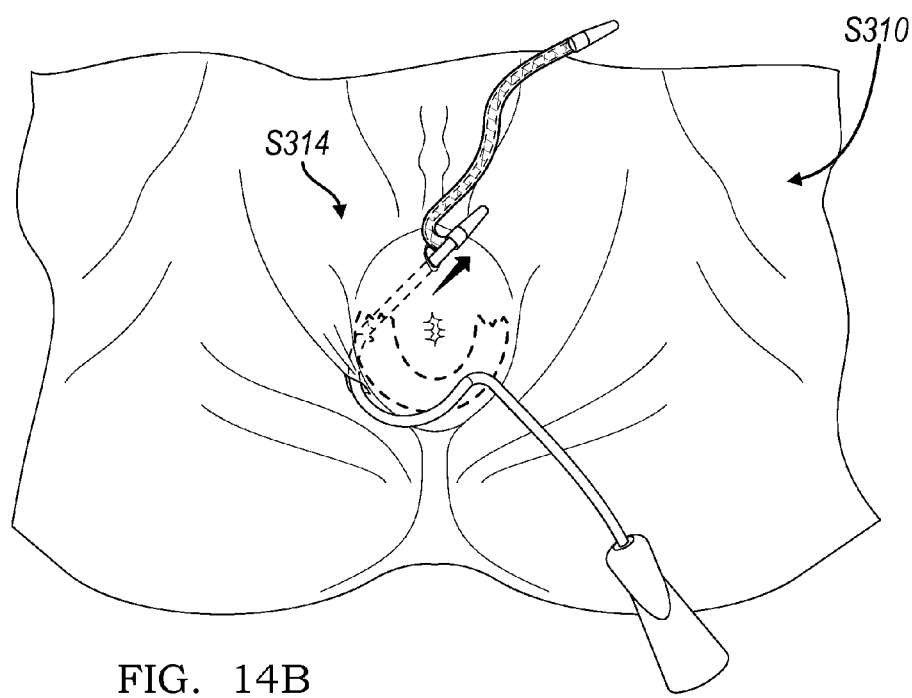
Figure 14C:
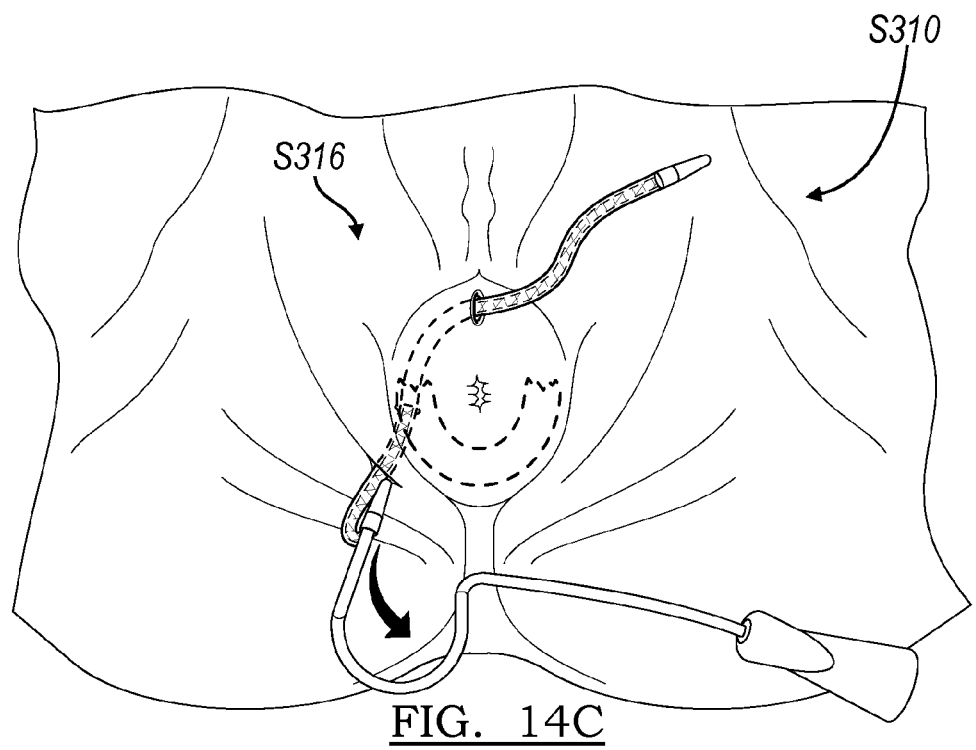
Figure 14D:
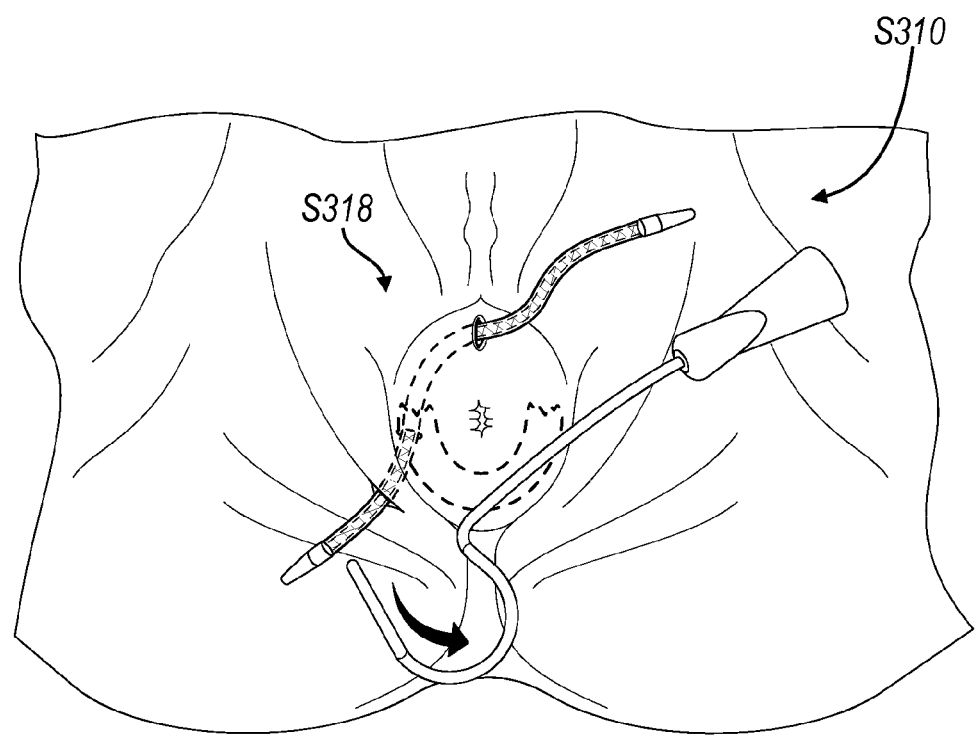
Figure 15A:
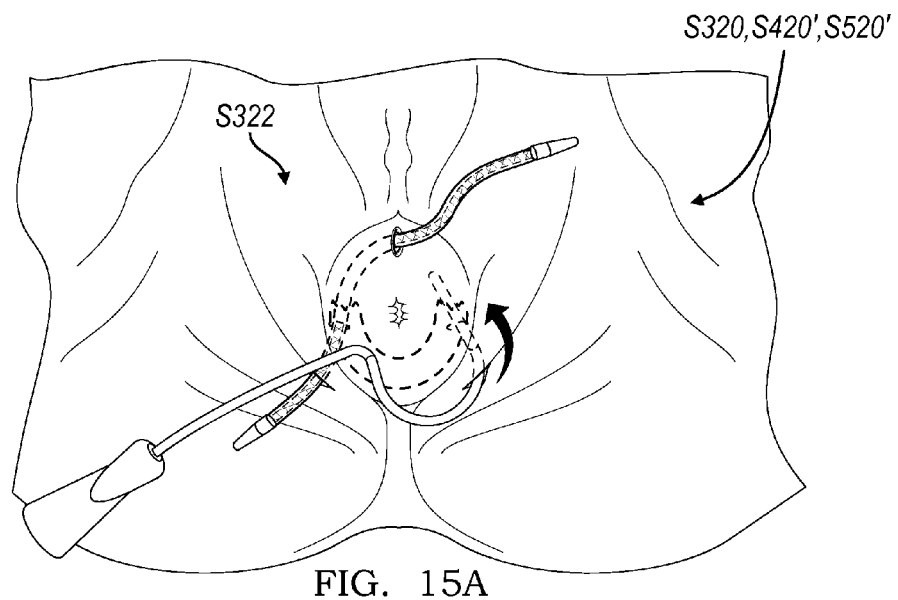
FIG. 15 is an illustration of the step of passing a second end of the sling through the sphincter at a second point of the pulling down variation of the method of implanting an anal sling.
Figure 15B:
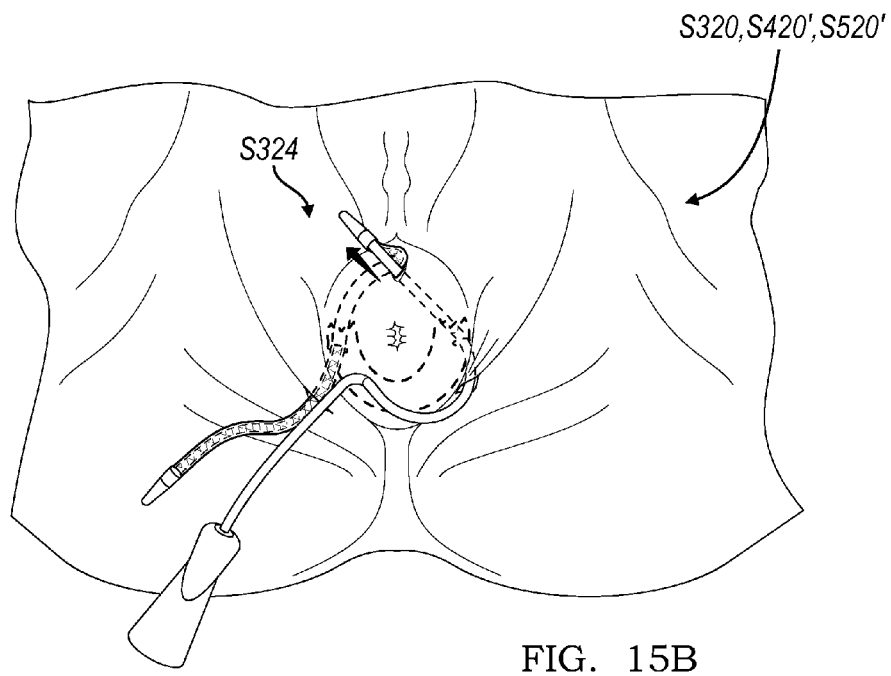
Figure 15C:
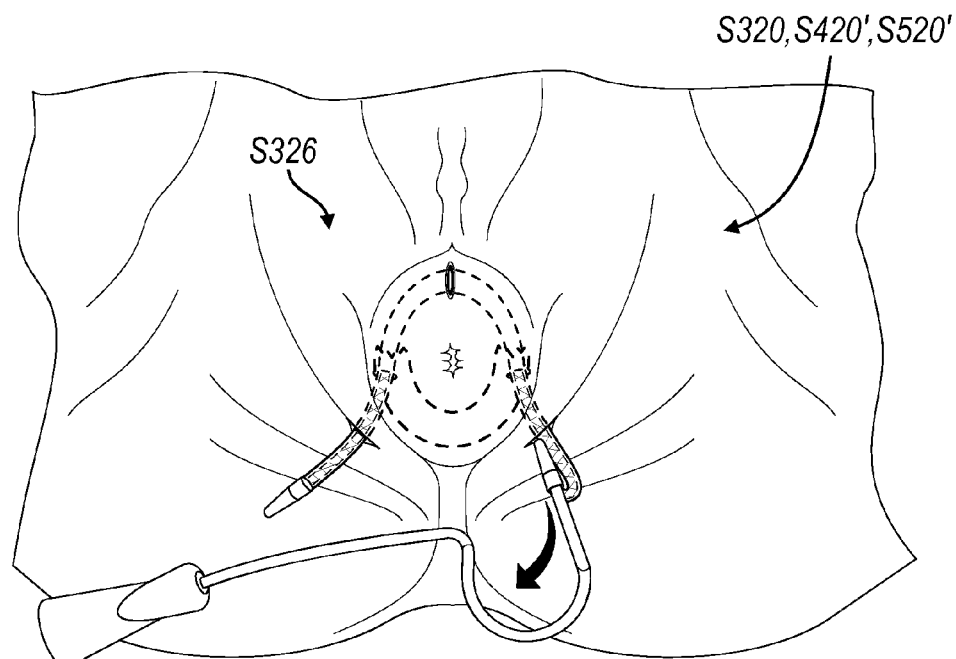
Figure 15D:
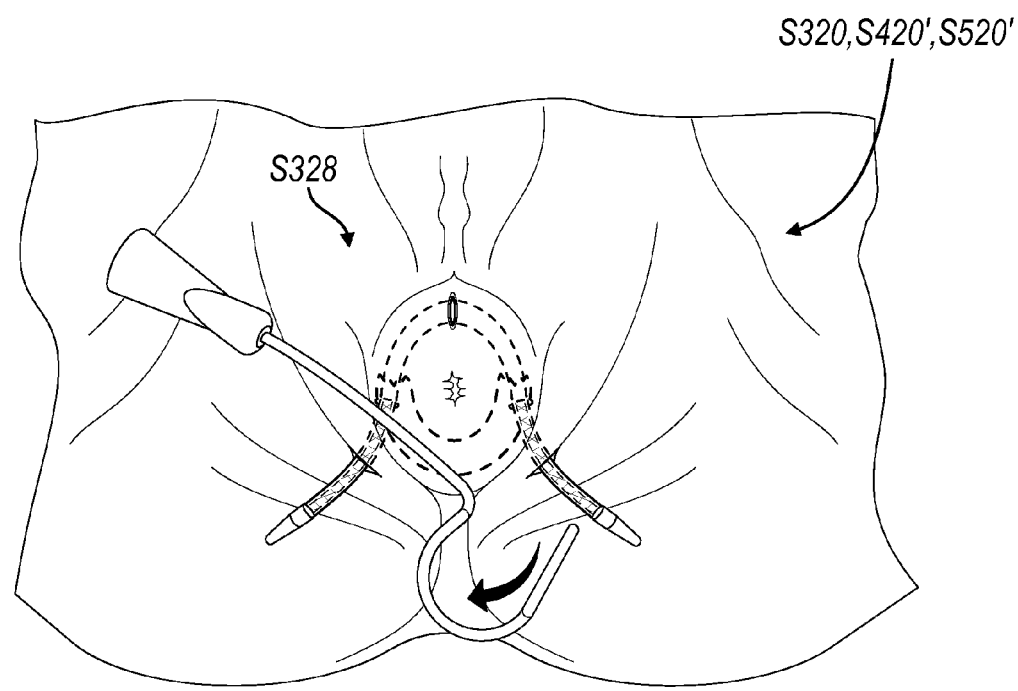
Figure 16A:
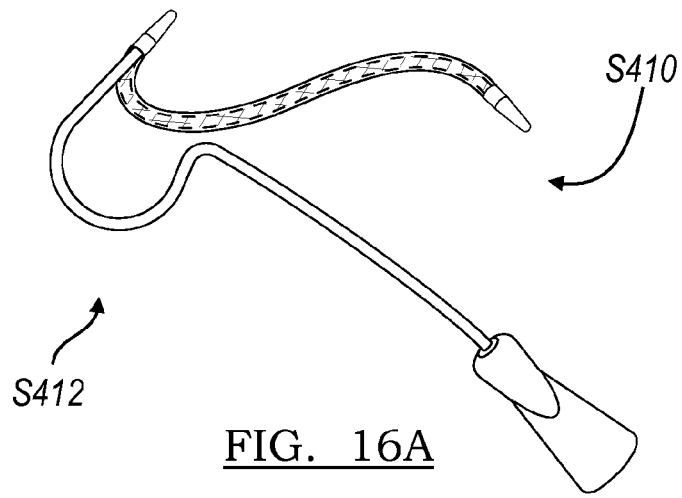
FIG. 16 is an illustration of the step of threading a first end of the sling through the sphincter at a first point of the pushing up variation of the method of implanting an anal sling.
Figure 16B:
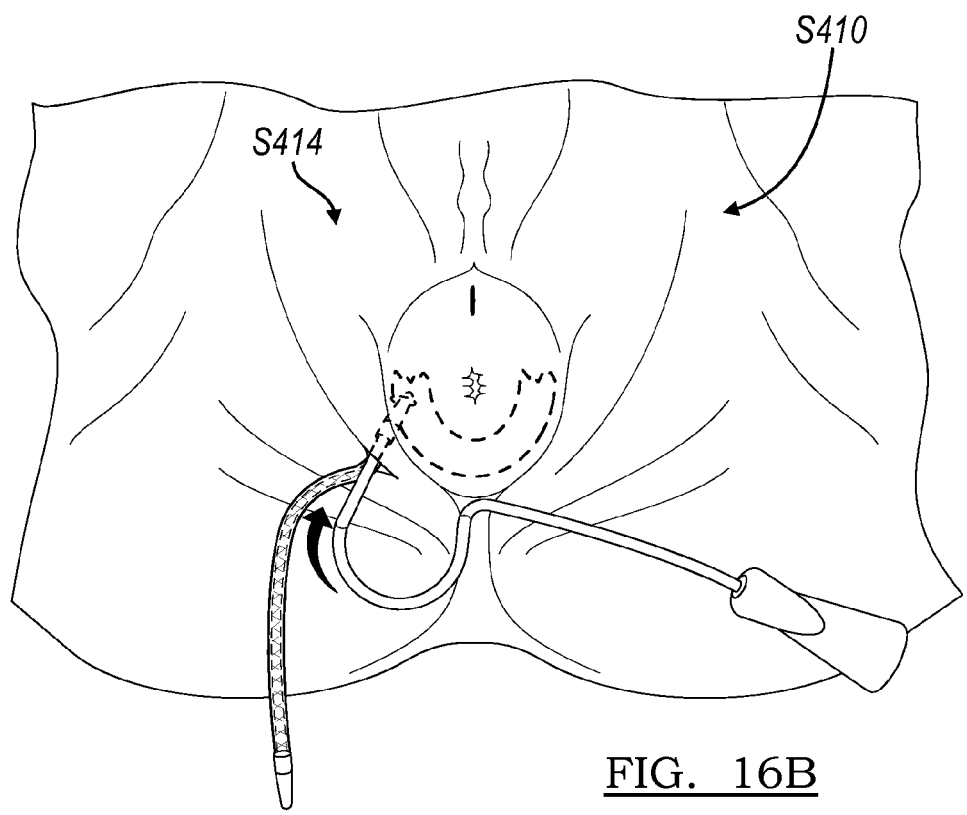
Figure 16C:
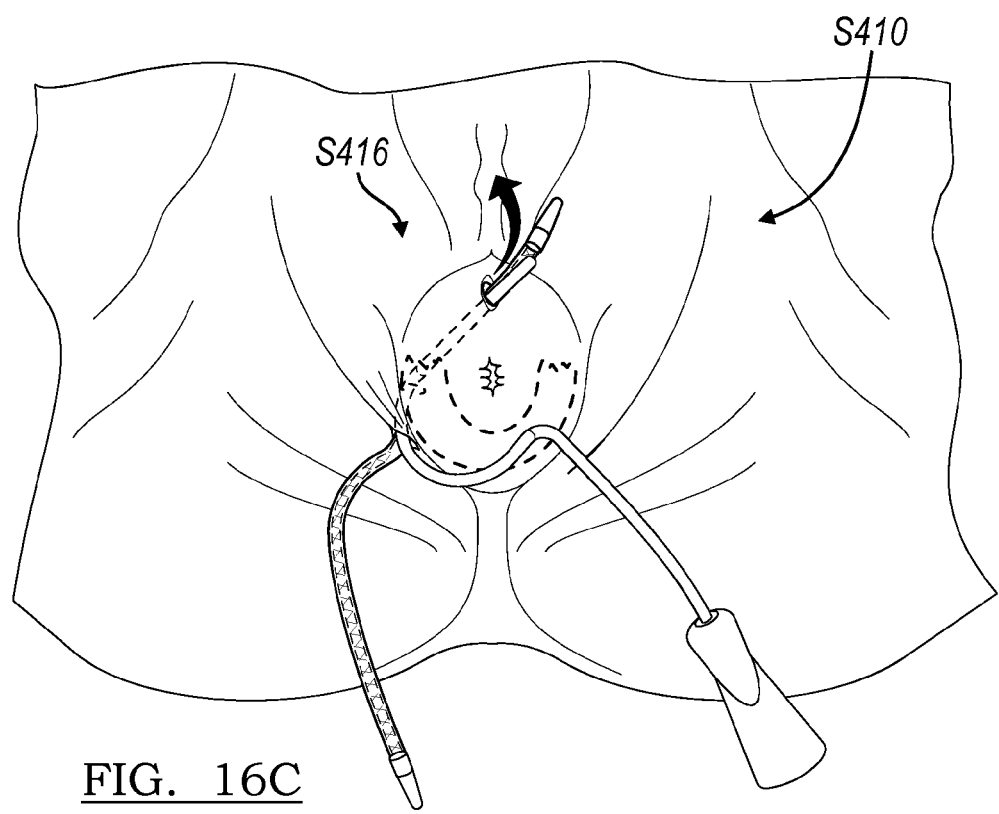
Figure 16D:
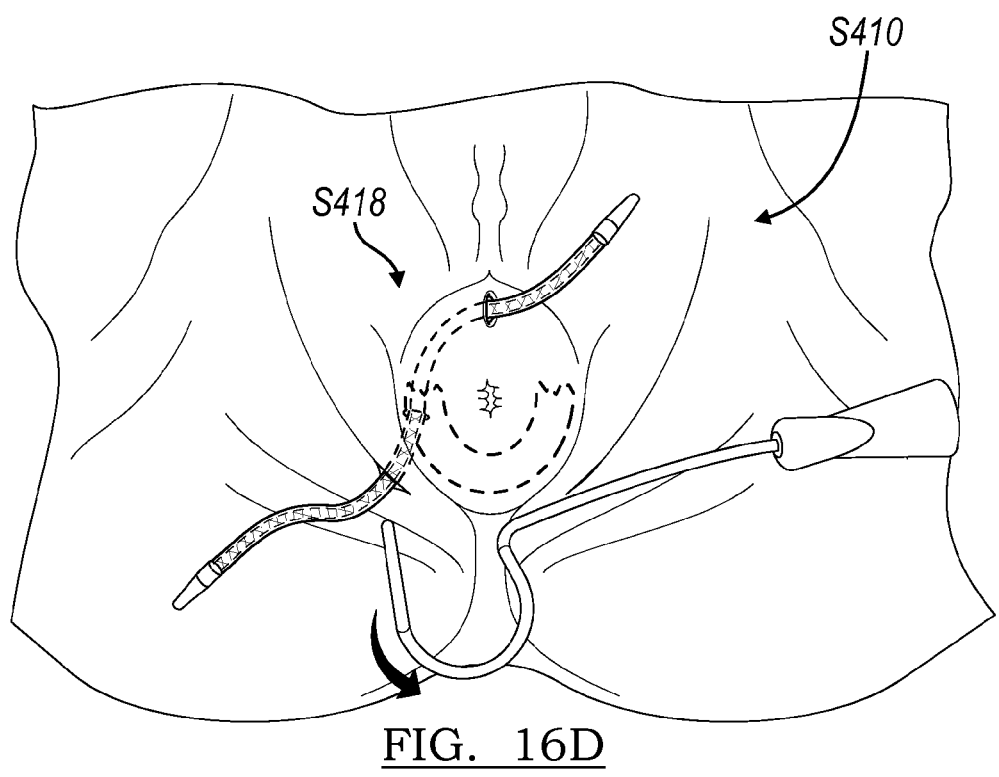
Figure 17A:
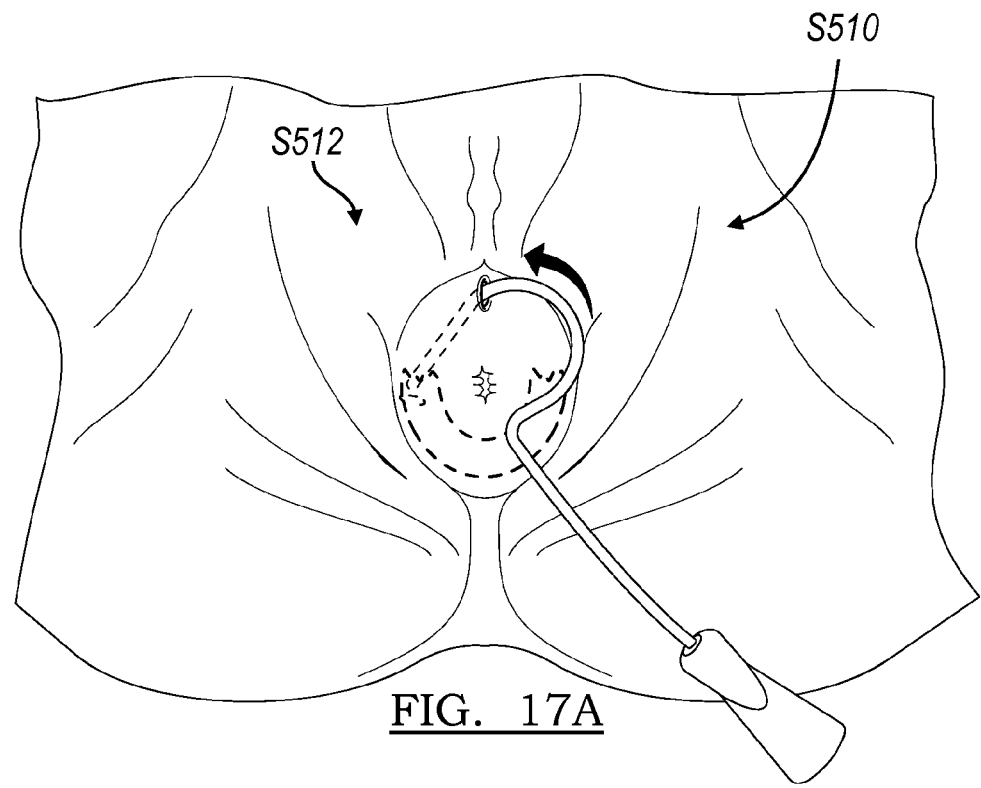
FIG. 17 is an illustration of the step of threading a first end of the sling through the sphincter at a second point of the pulling up variation of the method of implanting an anal sling.
Figure 17B:
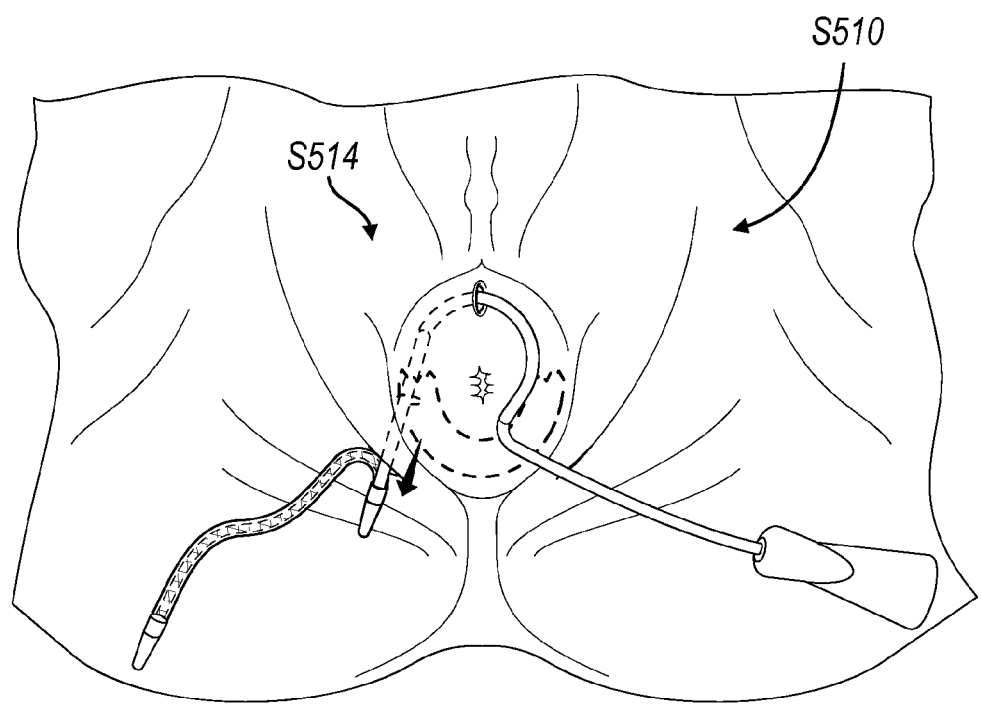
Figure 17C:
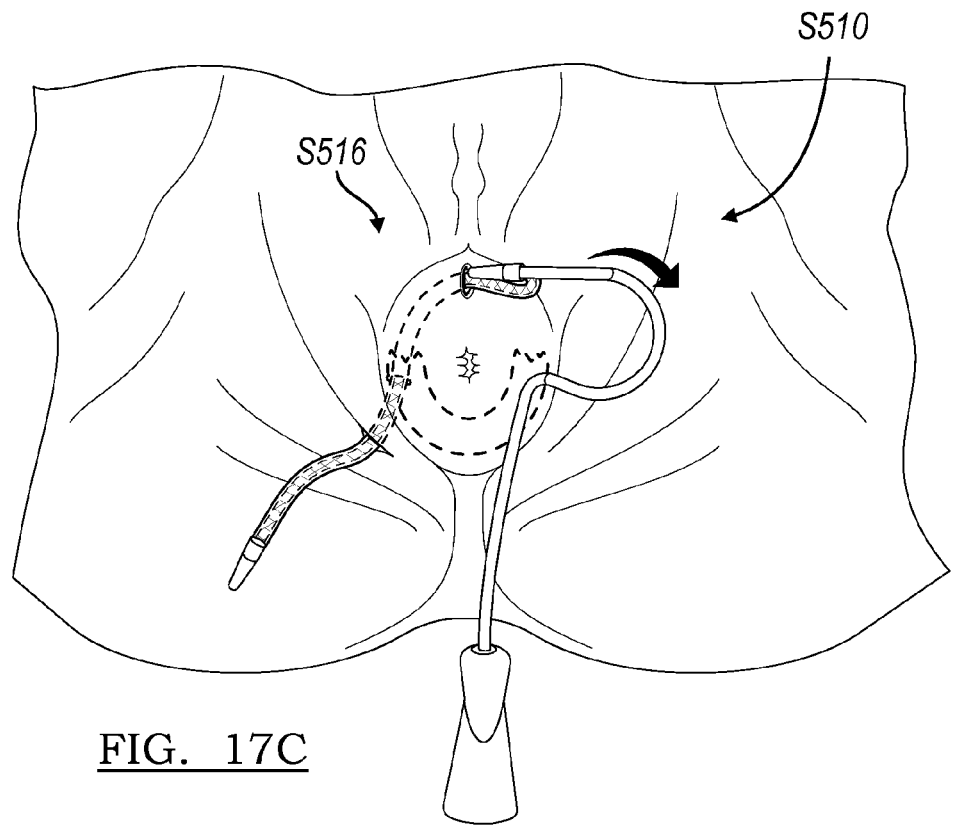
Figure 17D:
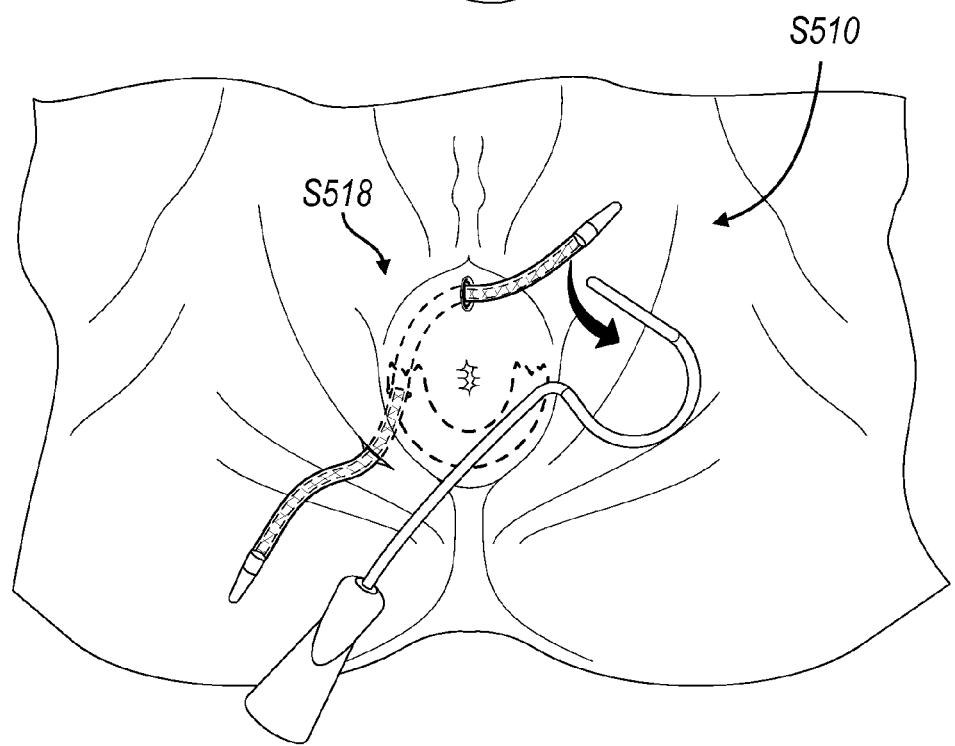

The method may further include Step S250, which includes closing incisions and functions to finish implantation of the sling. Step S250 preferably is performed for all incisions created during implantation of the sling, but may alternatively be performed for a portion of all incisions created during implantation of the sling, such as if some incisions are smaller and do not require surgical closure to aid healing. As shown in FIG. 13, Step S250 is preferably performed with sutures, staples, skin glue, and/or any suitable wound closure mechanism or technique. As an example, the incisions may be closed with absorbable sutures. The step of closing incisions may include trimming excess portion of the sling at the surface of the skin with scissors, blade, or another suitable cutting instrument.

2.2 Method of Implanting an Anal Sling—"Pulling Down"

The pulling down variation of the method of implanting an anal sling in an anal sphincter of a patient preferably includes the steps of: linking a first point on the anal sphincter and a second point on the anal sphincter, which includes passing a first end of the sling through the sphincter at a first point S310, and passing a second end of the sling through the anal sphincter at a second point S320; and tightening the sling over a defective portion of the anal sphincter S330. The first and second points on the anal sphincter are preferably located opposite to one another across the defective portion. The method may also include removing a sheath of the sling S340 and/or closing incisions S350.

Step S310, which includes passing a first end of the sling through the anal sphincter at a first point, functions to implant a portion of the sling in the anal sphincter in the patient. As shown in FIGS. 14A-14D, in the pulling down variation, Step 310 includes the following four substeps: passing a first needle tool into a tunnel that passes through the anal sphincter at a first point S312, wherein the first needle tool preferably enters the tunnel at a buttock incision created in the buttock of the patient and the first needle tool preferably exits the tunnel at a perineal incision created in the perineum of the patient; coupling the first needle tool to a first insertion tip on the first end of the sling S314; passing the first needle tool and first end of the sling through the tunnel and through the anal sphincter at the first point to exit out the buttock incision S316; and decoupling the first needle tool from the first end of the sling S318. Step S312 is preferably similar to Step S214, except that Step S312 is performed with the needle tool not attached to the first insertion tip and the first end of the sling, and Step S312 passes the first needle tool through the tunnel to exit out the perineal incision, in the opposite direction from that in Step S214. Step S314 is preferably identical to Step S212. Step S316 is preferably similar to Step S214, except Step S316 pulls the sling through the tunnel, while Step S214 pushes the sling through the tunnel. Step S318 is preferably identical to Step S216.

Step S320, which includes passing a second end of the sling through the anal sphincter at a second point, functions to implant a portion of the sling in the patient. As shown in FIGS. 15A-15D, in the pulling down variation of the step, the step of passing a second end of the sling includes the four substeps of: passing a second needle tool into a second tunnel that passes through the anal sphincter at a second point S322, wherein the second needle tool preferably enters the tunnel at a buttock incision created in the buttock of the patient and the second needle tool preferably exits the tunnel at a perineal incision created in the perineum of the patient; coupling the second needle tool to a second insertion tip on the second end of the sling S324; passing the second needle tool and second end of the sling through the tunnel to exit out the buttock incision S326; and decoupling the second needle tool from the second end of the sling S328. Steps S322, S324, S326 and S328 are preferably similar to Steps S312, S314, S316, and S318 respectively, except that Steps S322, S324, S326, and S328 are preferably mirrored versions of Steps S312, S314, S316, and S318, respectively.

Steps S330, S340, and S350 are preferably identical to Steps S230, S240 and S250, respectively, of the pushing down variation of the method.

2.3 Method of Implanting an Anal Sling—"Pushing Up"

The pushing up variation of the method of implanting an anal sling in an anal sphincter of a patient preferably includes the steps of: linking a first point on the anal sphincter and a second point on the anal sphincter, which includes passing a first end of the sling through the anal sphincter at a first point S410; threading a second end of the sling through a second end of the functional portion of the sphincter S420; and tightening the sling across a defective portion of the anal sphincter S430. The first and second points on the anal sphincter are preferably located opposite to one another across the defective portion. The method may also include removing the sheath of the sling S440 and/or closing incisions S450.

Step S410, which includes passing a first end of the sling through the anal sphincter at a first point, functions to implant a portion of the sling in the anal sphincter of the patient. As shown in FIGS. 16A-16D, in the pushing up variation, Step S410 includes the four substeps of: coupling a first needle tool to a first insertion tip on a first end of the sling S412; passing the first needle tool and first end of the sling into a tunnel that passes through the anal sphincter at a first point S414, in which the first needle tool preferably enters the tunnel at a buttock incision created in the buttock of the patient and the first needle tool preferably exits the tunnel at a perineal incision created in the perineum of the patient; decoupling the first needle from the first insertion tip S416; and withdrawing the first needle tool to exit out the buttock incision S418. Step S412 is preferably identical to Step S212. Step S414 is preferably similar to Step S214, except that Step S414 preferably pushes the first needle tool to exit out the perineal incision, in an opposite direction from that in Step S214. Step S416 is preferably identical to Step S216. Step S418 is preferably similar to Step S218, except that Step S418 passes the first needle tool in the opposite direction from that in Step S218.

Step S420, which includes threading a second end of the sling through the anal sphincter at a second point, functions to implant a second portion of the sling in the sphincter of patient. Step S420 may be identical to Step S220 of the pushing down variation, of the method, or may be identical to Step S320 of the pulling down variation of the method. Alternatively, Step S420 may be similar to Step S410, in which the second end of the sling is located on a separate half of the sling, and the method further includes joining the second end of the sling with the first end of the sling to form a single, longer sling.

Steps S430, S440, and S450 are preferably identical to Steps S230, S240, and S250, respectively, of the pushing down variation of the method.

2.4 Method of Implanting an Anal Sling—"Pulling Up"

The pulling up variation of the method of implanting an anal sling in an external anal sphincter of a patient preferably includes the steps of: linking a first point on the anal sphincter and a second point on the anal sphincter, which includes passing a first end of the sling through the anal sphincter at a first point S510 and passing a second end of the sling through a second end of the anal sphincter at a second point S520; and tightening the sling across a defective portion of the anal sphincter S530. The first and second points on the anal sphincter are preferably located opposite to one another across the defective portion. The method may also include removing the sheath of the sling S540 and/or closing incisions S550.

Step S510, which includes passing a first end of the sling through the anal sphincter at a first point, functions to implant a portion of the sling in the sphincter of the patient. As shown in FIGS. 17A-17D, in the pulling up variation, S510 includes the four substeps of: passing a first needle tool into a tunnel that passes through the anal sphincter at a first point S512, in which the first needle tool preferably enters the tunnel at a perineal incision created in the perineum of the patient and the first needle tool preferably exits the tunnel at a buttock incision created in the buttock of the patient; coupling the first needle tool to a first insertion tip on the first end of the sling S514; passing the first needle tool and first end of the sling through the tunnel to exit out the perineal incision S516; and decoupling the first needle tool from the first end of the sling S518. Step S512 is preferably similar to Step S312, except that Step S512 passes the needle to exit out the buttock incision, in an opposite direction from that in Step S312. Step S514 is preferably identical to Step S314. Step S516 is preferably similar to Step S316, except that Step S516 passes the first needle tool to exit out the perineal incision, in the opposite direction from that in Step S316. Step S518 of decoupling the first needle tool from the first end of the sling is preferably identical to Step S318.

Step S520, which includes threading a second end of the sling through the anal sphincter at a second point, functions to implant a second portion of the sling in the sphincter in the patient. Step S520 may be identical to Step S220 of the pushing down variation of the method, or may be identical to Step S320 of the pulling down variation of the method. Alternatively, Step S520 may be similar to Step S510, in which the second end of the sling is located on a separate half of the sling, and the method further includes joining the second end of the sling with the first end of the sling to form a single, longer sling.

Steps S530, S540, and S550 are preferably identical to Steps S230, S240, and S250, respectively, of the pushing down variation of the method.

2.5 Alternative Methods of Implanting an Anal Sling

Figure 18A:
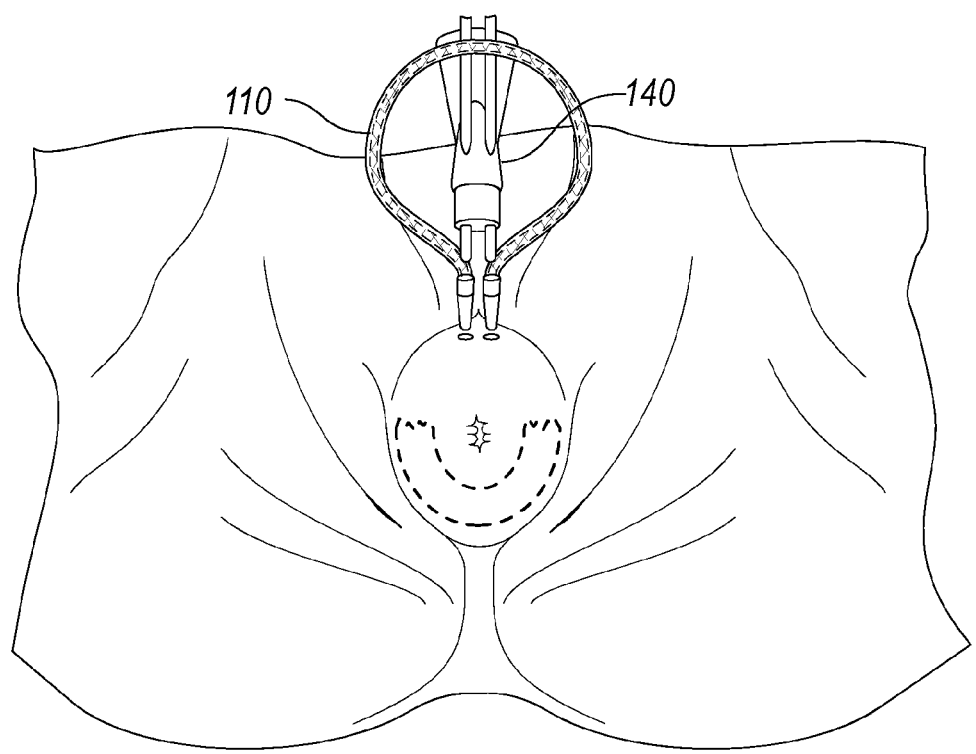
FIGS. 18-20 are first, second, and third alternative embodiments, respectively, of the method of implantation of an anal sling.
Figure 18B:
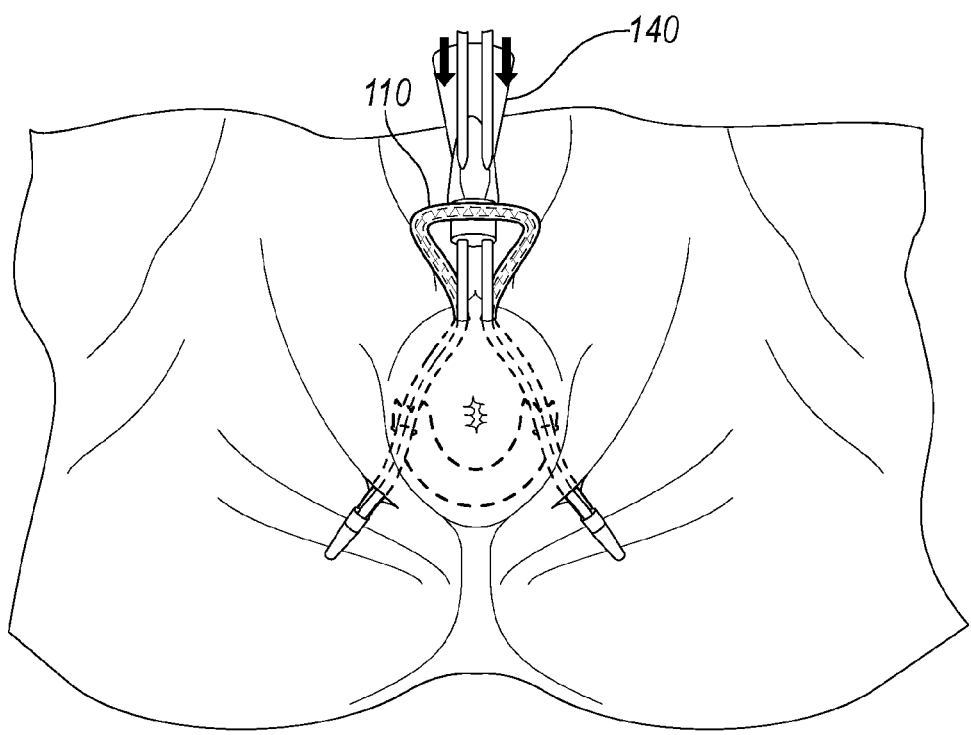

Various alternative embodiments of the method are similar to the above described variations, except as noted below. In a first alternative embodiment of the method, the first and second ends of the sling may be simultaneously threaded or passed through the sphincter at the first and second points, respectively. As shown in FIGS. 18A and 18B, the first alternative embodiment of the method may be performed with the use of an expandable branched needle tool 140 that enters the perineal incision and simultaneously passes branches coupled to the first and second insertion tips of the sling through tunnels that pass through the first and second points and may exit out a pair of buttock incisions.

Figure 19A:
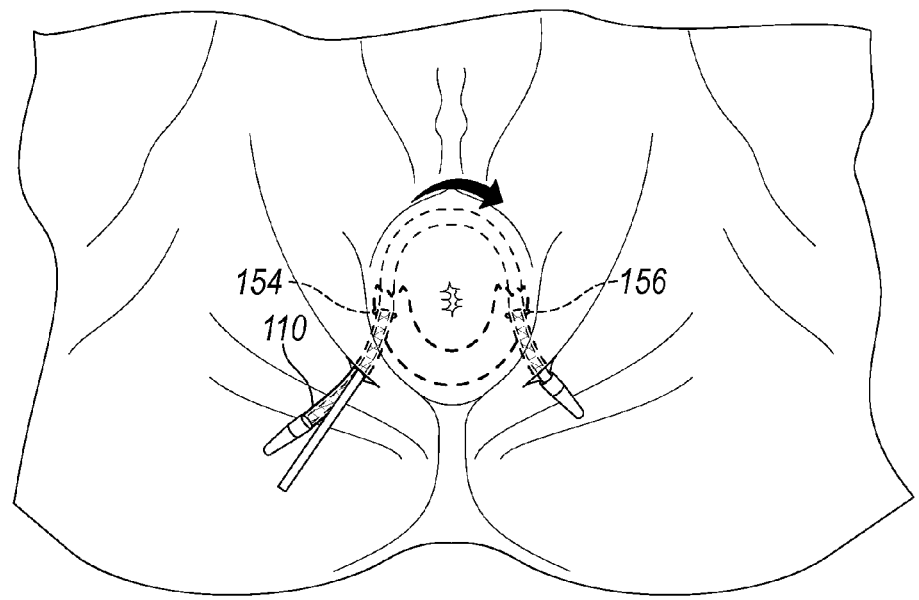
Figure 19B:
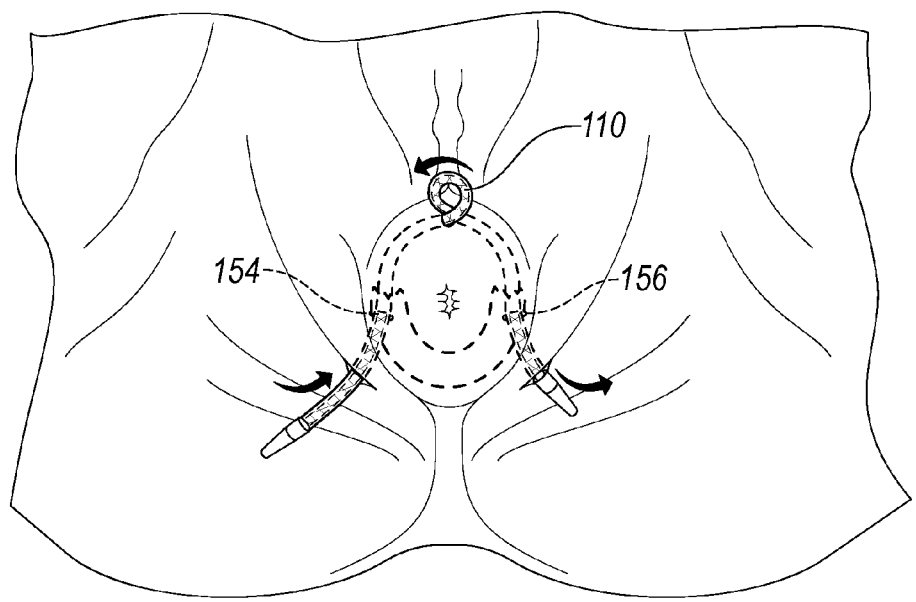

As shown in FIGS. 19A and 19B, in a second alternative embodiment, a single curved needle tool or another suitable tool may be used to sequentially thread the first and second points. The sling may be implanted in a passageway that minimally include entering one buttock incision, passing through the sphincter the first and second point, and exiting another buttock incision.

Figure 20A:
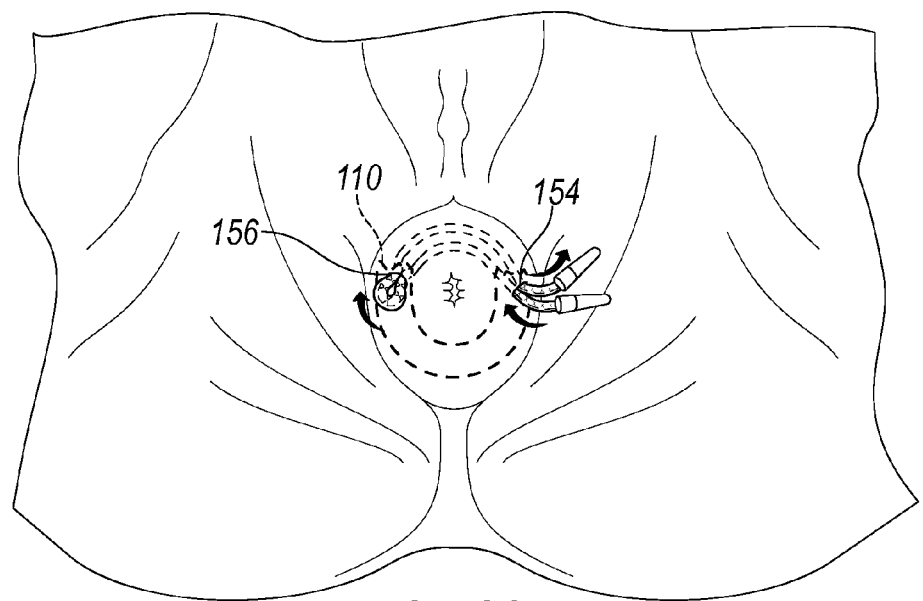
Figure 20B:
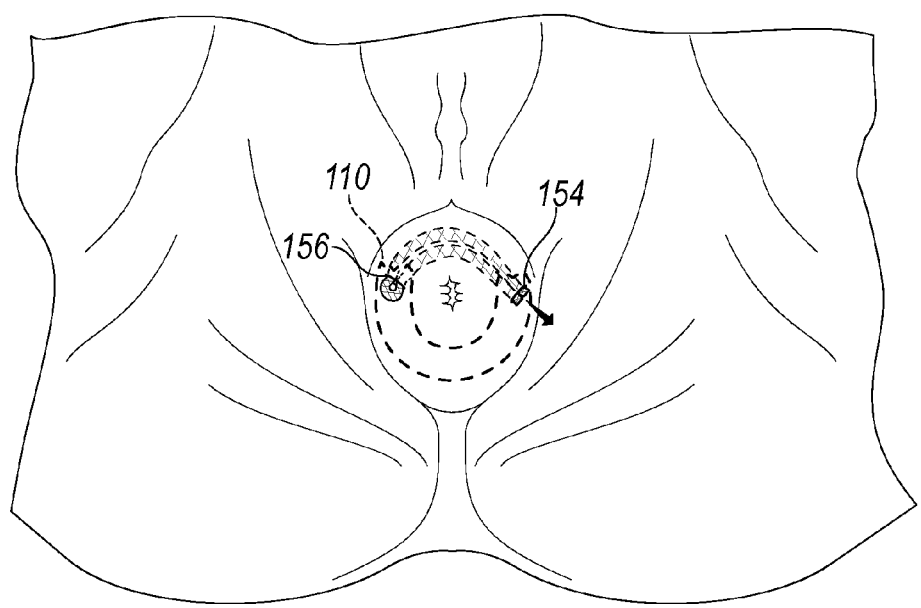
Figure 21:
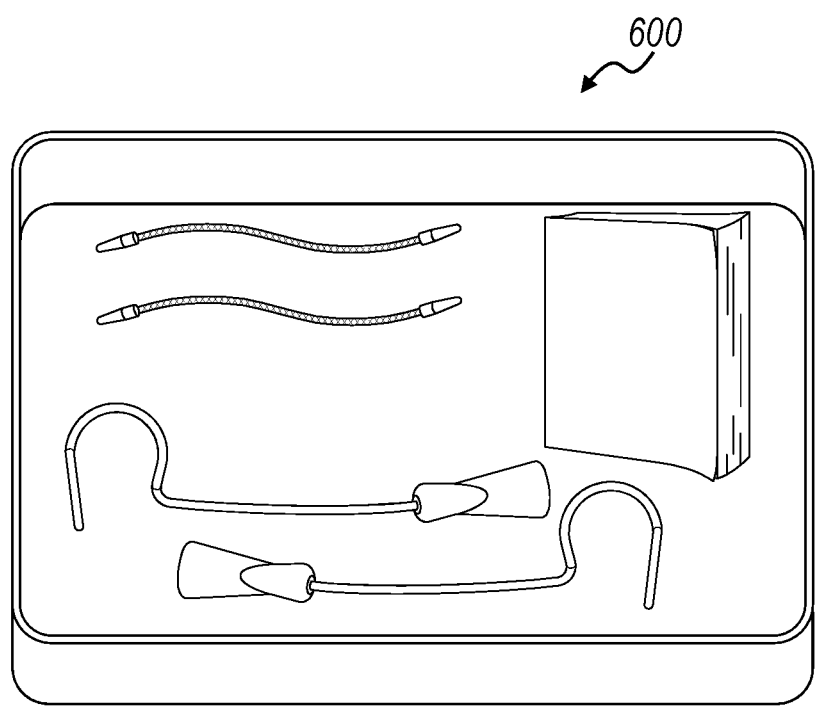
FIG. 21 is an illustration of the preferred embodiment of the method of packaging an anal sling system.

As shown in FIGS. 20A and 20B, in a third alternative embodiment, the sling may be passed through the sphincter at the first point 154, over the perineum in a forward direction, through the sphincter at the second point 156, and over the perineum in a reverse direction, then tightened across the defective portion of the anal sphincter, such as by pulling on one end of the sling while holding the other.

Other embodiments of the method include every combination and permutation of the described steps of the described variations, including the steps of threading the first end of the sling through a first end of the functional portion of the sphincter and threading the second end of the sling through a second end of the functional portion of the sphincter.

3. Method of Packaging an Anal Sling System

As shown in FIG. 17, a method of packaging an anal sling system preferably includes any combination of the following steps, or any suitable steps: providing an anal sling; providing a needle tool set having a left-side needle tool and a right-side needle tool; providing instructions describing how to perform a method of implanting an anal sling; and placing the anal sling, the needle tool set, and instructions in a package. The anal sling, left-side needle tool, and right-side needle tool are preferably similar to those described in the above Section 1. The instructions preferably include one or more of the variations described in the above Section 2. The anal sling, the needle tool set having a left-side needle tool and a right-side needle tool, and instructions describing how to perform a method of implanting an anal sling can be combined and provided as a "kit" 600.

As a person skilled in the art will recognize from the previous detailed description and from the figures and claims, modifications and changes can be made to the preferred embodiments of the invention without departing from the scope of this invention defined in the following claims.

I claim:

1. A method of implanting an anal sling to treat fecal incontinence in a patient having an anal sphincter with a defective portion, comprising the steps of:
    linking a first point on the anal sphincter and a second point on the anal sphincter, wherein the second point opposes the first point across the defective portion of the anal sphincter, comprising:
    creating a perineal incision;
    coupling a first end of the anal sling to a first-side needle tool;
    passing the first-side needle tool and the first end of the anal sling through a first passageway, connected to the perineal incision, through the superficial surface of the wall of the anal sphincter at the first point;
    coupling a second end of the anal sling to a second-side needle tool; and
    passing the second-side needle tool and the second end of the anal sling through a second passageway, connected to the perineal incision, through the superficial surface of the wall of the anal sphincter at the second point; and
    tightening the anal sling across the defective portion of the anal sphincter.

2. The method of claim 1, wherein the step of passing the first-side needle tool includes pushing the first-side needle tool and the first end of the anal sling through the first passageway through the superficial surface of the wall of the anal sphincter at the first point.

3. The method of claim 2, wherein the step of pushing the first-side needle tool includes pushing the first-side needle tool and the first end of the anal sling through the perineal incision.

4. The method of claim 3, wherein the step of pushing the first-side needle tool further includes pushing the first-side needle tool and the first end of the anal sling through a buttock incision coupled to the first passageway.

5. The method of claim 2, wherein the step of pushing the first-side needle tool includes pushing the first side needle tool and the first-end of the anal sling through a buttock incision coupled to the first passageway and through the perineal incision.

6. The method of claim 2, wherein the step of passing the second-side needle tool includes pushing the second-side needle tool and the second end of the anal sling through the perineal incision.

7. The method of claim 6, further comprising laying the anal sling flat on the anal sphincter in the perineal incision.

8. The method of claim 7, further comprising the step of widening the width of the perineal incision substantially equal to a width of the anal sling.

9. The method of claim 2, further comprising the step of passing the second-side needle tool through a buttock incision coupled to the second passageway in a forward direction, performed before the step of coupling the second end of the anal sling to the second-side needle tool; wherein the step of passing the second-side needle tool includes pulling the second-side needle tool and the second end of the anal sling through the buttock incision in a reverse direction.

10. The method of claim 2, wherein the step of linking a first point on the anal sphincter and a second point on the anal sphincter includes linking a first point on an external anal sphincter and a second point on the external anal sphincter.

11. The method of claim 2, further comprising the step of removing a sheath that encloses the anal sling.

12. The method of claim 1, wherein the step of passing the first-side needle tool includes pulling the first-side needle tool and the first end of the anal sling through the first passageway through the superficial surface of the wall of the anal sphincter at the first point.

13. The method of claim 12, further comprising passing the first-side needle tool through a buttock incision coupled to the first passageway in a forward direction, performed before coupling the first end of the anal sling to the first-side needle tool; wherein pulling the first-side needle tool includes pulling the first-side needle tool and first end of the anal sling through the buttock incision in a reverse direction.

14. The method of claim 12, further comprising the step of passing the first-side needle tool through the perineal incision in a forward direction through the first passageway, performed before the step of coupling the first end of the anal sling to the first-side needle tool; wherein the step of pulling the first-side needle tool includes the first-side needle tool and the first end of the anal sling through the perineal incision in a reverse direction.

15. The method of claim 12, wherein the step of passing the second-side needle tool and the second end of the anal sling through the second passageway includes pushing the second-side needle tool and the second end of the anal sling through the perineal incision.

16. The method of claim 12, further comprising passing the second-side needle tool through a buttock incision coupled to the second passageway in a forward direction, performed before coupling the second end of the anal sling to the second-side needle tool; wherein passing the second-side needle tool includes pulling the second-side needle tool and the second end of the anal sling through the buttock incision in a reverse direction.

17. The method of claim 16, further comprising laying the anal sling flat on the anal sphincter in the perineal incision.

18. The method of claim 17, further comprising the step of widening the perineal incision to be substantially equal to a width of the anal sling.

19. The method of claim 12, further comprising the step of removing a sheath that encloses the anal sling.

20. The method of claim 1, wherein the perineal incision is created at an anterior portion of the perineum.

21. The method of claim 1, wherein the perineal incision is created at a posterior fourchette of the vagina.

22. The method of claim 1, wherein the first point and the second point are angularly displaced around a longitudinal axis of the anal sphincter by greater than 180 degrees.

23. The method of claim 1, wherein through the superficial surface of the wall of the anal sphincter at the first point comprises into the superficial surface of the wall of the anal sphincter at the first point, and through the superficial surface of the wall of the anal sphincter at the second point comprises out of the superficial surface of the wall of the anal sphincter at the second point.

24. The method of claim 1, wherein through the superficial surface of the wall of the anal sphincter at the first point comprises into the superficial surface of the wall of the anal sphincter at the first point and out of the superficial surface of the wall of the anal sphincter substantially close to the first point.

25. The method of claim 1, wherein through the superficial surface of the wall of the anal sphincter at the second point comprises into the superficial surface of the wall of the anal sphincter at the second point and out of the superficial surface of the wall of the anal sphincter substantially close to the second point.

26. The method of claim 1, further comprising linking a third point on the anal sphincter and a fourth point on the anal sphincter with a second anal sling.

27. The method of claim 26, wherein the first anal sling and second anal sling overlap at at least one point.

28. The method of claim 1, wherein at least one of the first passageway and the second passageway is not coupled to a buttock incision.

29. The method of claim 1, further comprising creating a left buttock incision coupled to the first passageway, and a right buttock incision coupled to the second passageway.

30. The method of claim 29, wherein at least one of the left buttock incision and the right buttock incision is created within 3 cm lateral to the anal sphincter and within 3 cm posterior to the anal sphincter.

31. The method of claim 1, wherein at least one of the first passageway through the superficial surface of the wall of the anal sphincter and the second passageway through the superficial surface of the wall of the anal sphincter is a passageway through the internal anal sphincter.

32. The method of claim 1, wherein at least one of the first passageway through the superficial surface of the wall of the anal sphincter and the second passageway through the superficial surface of the wall of the anal sphincter is a passageway through the external anal sphincter.

33. The method of claim 1, wherein at least one of the first passageway through the superficial surface of the wall of the anal sphincter and the second passageway through the superficial surface of the wall of the anal sphincter passes through a deep surface of the wall of the anal sphincter.

34. A method of implanting an anal sling to treat fecal incontinence in a patient having an anal sphincter with a defective portion, comprising the steps of:
linking a first point on the anal sphincter and a second point on the anal sphincter, wherein the second point opposes the first point across the defective portion of the anal sphincter, including:
threading an end of the anal sling, coupled to a needle tool, through the superficial surface of the wall of the anal sphincter at the first point;
passing the end of the anal sling over the perineum of the patient in a forward direction;
threading the end of the anal sling through the superficial surface of the wall of the anal sphincter at the second point; and
passing the end of the anal sling over the perineum of the patient in a reverse direction; and
tightening the anal sling across the defective portion of the anal sphincter.

35. The method of claim 34, wherein threading an end of the anal sling through the superficial surface of the wall of the anal sphincter comprises threading an end of the anal sling through a portion of at least one of the internal anal sphincter and the external anal sphincter.

36. A method of implanting an anal sling in a patient having an anal sphincter with a defective portion, comprising the steps of:
linking a first point on the anal sphincter and a second point on the anal sphincter, wherein the second point opposes the first point across the defective portion of the anal sphincter, including:
passing a first end of the anal sling, coupled to a first-side needle tool, through the superficial surface of the wall of the anal sphincter at the first point; and passing a second end of the anal sling, coupled to a second-side needle tool, through the superficial surface of the wall of the anal sphincter at the second point; and tightening the anal sling across the defective portion of the anal sphincter.

* * * * *